(12) United States Patent
Oh et al.

(10) Patent No.: US 9,180,101 B2
(45) Date of Patent: Nov. 10, 2015

(54) PHARMACEUTICAL COMPOSITION SIMULTANEOUSLY HAVING RAPID-ACTING PROPERTY AND LONG-ACTING PROPERTY

(75) Inventors: Dong-Joon Oh, Suwon-si (KR); Byoung-Ki Kim, Suwon-si (KR); Byung-Kwan Moon, Hwaseong-si (KR); Ji-Seok Yoo, Suwon-si (KR); Dae-Hee Shin, Seoul (KR); Byung-Hwan Ryoo, Seongnam-si (KR)

(73) Assignee: YUNGJIN PHARM CO., LTD., Seoul (KR)

( * ) Notice: Subject to any disclaimer, the term of this patent is extended or adjusted under 35 U.S.C. 154(b) by 0 days.

(21) Appl. No.: 13/108,050

(22) Filed: May 16, 2011

(65) Prior Publication Data

US 2011/0217374 A1  Sep. 8, 2011

Related U.S. Application Data

(63) Continuation of application No. PCT/KR2010/006910, filed on Oct. 8, 2010.

(30) Foreign Application Priority Data

Oct. 9, 2009 (KR) .................. 10-2009-0096315
Oct. 30, 2009 (KR) .................. 10-2009-0104248

(51) Int. Cl.
*A61K 9/22* (2006.01)
*A61K 38/00* (2006.01)
*A61K 9/50* (2006.01)

(52) U.S. Cl.
CPC ..................... *A61K 9/5084* (2013.01)

(58) Field of Classification Search
None
See application file for complete search history.

(56) References Cited

U.S. PATENT DOCUMENTS

| | | | |
|---|---|---|---|
| 4,820,522 A | 4/1989 | Radebaugh et al. | |
| 6,669,955 B2 * | 12/2003 | Chungi et al. | 424/464 |
| 6,682,759 B2 | 1/2004 | Lim et al. | |
| 7,387,793 B2 * | 6/2008 | Venkatesh et al. | 424/489 |
| 2001/0046964 A1 * | 11/2001 | Percel et al. | 514/29 |
| 2002/0142034 A1 | 10/2002 | Shimizu et al. | |
| 2003/0215496 A1 * | 11/2003 | Patel et al. | 424/452 |
| 2006/0051421 A1 | 3/2006 | Shterman | |
| 2008/0175910 A1 | 7/2008 | Andre et al. | |
| 2008/0292701 A1 | 11/2008 | Shimizu | |
| 2008/0305165 A1 | 12/2008 | Noh et al. | |
| 2009/0022798 A1 * | 1/2009 | Rosenberg et al. | 424/472 |
| 2010/0047341 A1 | 2/2010 | Kim et al. | |
| 2010/0316709 A1 | 12/2010 | Kurasawa et al. | |
| 2011/0081412 A1 | 4/2011 | Shimizu | |
| 2014/0271856 A1 | 9/2014 | Shimizu et al. | |

FOREIGN PATENT DOCUMENTS

| | | |
|---|---|---|
| CN | 1785167 | 6/2006 |
| CN | 101015519 | 8/2007 |
| CN | 101023932 | 8/2007 |
| GB | 1019146 | 2/1966 |
| JP | 2000-281564 | 10/2000 |
| JP | 2003-503341 | 1/2003 |
| JP | 2006-124385 | 5/2006 |
| JP | 2007-223927 | 9/2007 |
| JP | 2008-502740 | 1/2008 |
| JP | 2009-524651 | 7/2009 |
| KR | 10-2004-0079980 | 9/2004 |
| KR | 10-2007-0078625 | 8/2007 |
| KR | 10-2007-0085155 | 8/2007 |
| KR | 10-2008-0032616 | 4/2008 |
| WO | 00/13678 | 3/2000 |
| WO | 02/087549 | 11/2002 |
| WO | 2006/036007 | 4/2006 |
| WO | 2007/086692 | 8/2007 |
| WO | 2008/044862 | 4/2008 |
| WO | 2008/061226 | 5/2008 |
| WO | WO 2008054121 A1 * | 5/2008 |
| WO | 2008-081891 | 7/2008 |

OTHER PUBLICATIONS

Chinese Patent Office, Office Action of the corresponding application (Chinese Patent Application No. 201080045422.0) (Jul. 29, 2013).
European Patent Office, European Search Report of Application No. 10825134.9 dated Jan. 23, 2014.

* cited by examiner

*Primary Examiner* — Jeffrey T Palenik
(74) *Attorney, Agent, or Firm* — Lex IP Meister, PLLC

(57) ABSTRACT

Disclosed is a pharmaceutical composition simultaneously having a rapid acting property and a long-acting property, comprising a sustained-release part coated with a water-insoluble polymer on the surface, comprising a first active pharmaceutical ingredient, at least one release control base selected from the group consisting of water-insoluble polymer, and water-soluble viscous polymer, and a pharmaceutically acceptable carrier; and, an immediate release part comprising a second active pharmaceutical ingredient and a pharmaceutically acceptable carrier. The pharmaceutical composition exhibits independent release properties of the immediate release part and the sustained-release part by coating the surface of the sustained-release part comprising an active pharmaceutical ingredient, a release control base and a pharmaceutically acceptable carrier with a water-insoluble polymer to separate it from the immediate release part, and it may be prepared by a relatively simple process without specification limitation to the contents and the kinds of usable pharmaceutically active ingredients.

7 Claims, 8 Drawing Sheets

PHARMACEUTICAL COMPOSITION SIMULTANEOUSLY HAVING RAPID-ACTING PROPERTY AND LONG-ACTING PROPERTY

CROSS-REFERENCE TO RELATED APPLICATIONS

This is a continuation of international application no. PCT/KR2010/006910 filed on Oct. 8, 2010, which claims all benefits accruing under 35 U.S.C. §119 from Korean Patent Application Nos. 10-2009-0096315 filed on Oct. 9, 2009 and 10-2009-0104248 filed on Oct. 30, 2009 earlier filed in the Korean Intellectual Property Office, the entire contents of which are incorporated herein by reference.

BACKGROUND OF THE INVENTION (a) Field of the Invention

This disclosure relates to a pharmaceutical composition simultaneously having a rapid-acting property and a long-acting property. The pharmaceutical composition exhibits independent release properties of an immediate release part and a sustained-release part, and it may be prepared by a relatively simple process without limitation to the composition and the kinds of usable active pharmaceutical ingredients (API).

(b) Description of the Related Art

Currently, according to the progress of preparation technologies, developments of technologies for sustained-release of various drugs are under progress in order to improve compliance of patients. A sustained-release preparation decreases the number of administration while effectively inducing potential effects of drugs by maintaining pharmaceutical effects, compared to an immediate-release preparation, and it has a lot of advantages in terms of effectiveness and safety such as reduction in side-effects or toxicity. However, for analgesics, etc. requiring immediate effects, a rapid acting property of rapidly reaching effective blood concentration to exhibit analgesic effect, etc. after administration is also required. Thus, a development of preparation simultaneously having a rapid-acting property and a long-acting property is required.

A representative preparation simultaneously having a rapid-acting property and a long-acting property includes Tylenol ER currently marketed by Janssen (U.S. Pat. No. 4,820,522), which simultaneously contains a determined drug dose containing a wicking agent and an erosion promoter in an immediate-release drug layer, and a powder composition and a determined drug dose containing an active matrix binder (hydroxyethylcellulose) and a wicking agent (microcrystalline cellulose) in a sustained-release drug layer, and is a dual-layered tablet prepared using a specific tableting machine.

As the existing technologies having the immediate-release part and the sustained-release part, a multi layer tablet prepared by depositing an immediate-release part and a sustained-release part, a core tablet prepared by forming a sustained-release part and then inserting it in an immediate-release part and dually tableting, an osmotic pump tablet, and spherical granules prepared by extrusion and spheronization have been reported.

However, according to the existing technologies, specific equipments are required and the process is complicated. And, since in the existing technologies, both the immediate-release part and the sustained-release part are tableted in the form of a matrix or compression-molded, disintegration or release of the immediate-release part may be delayed due to the base contained in the sustained-release part, and thus, it may be difficult that the immediate-release part and the sustained-release independently exhibit release properties. Furthermore, they are difficult to be applied for a drug requiring high content.

SUMMARY OF THE INVENTION

Accordingly, the inventors studied on the pharmaceutical composition that may be prepared by a simple process, has no limitation to the contents and the kinds of active active pharmaceutical ingredients, and may exhibit independent release properties of the immediate release part and the sustained-release part, and completed the invention.

Therefore, it is an object of the present invention to provide a pharmaceutical composition that may be prepared by a simple process, has no limitation to the contents and the kinds of active pharmaceutical ingredients, and may exhibit independent release properties of the immediate release part and the sustained-release part.

DETAILED DESCRIPTION OF THE EMBODIMENTS

Figure 1:
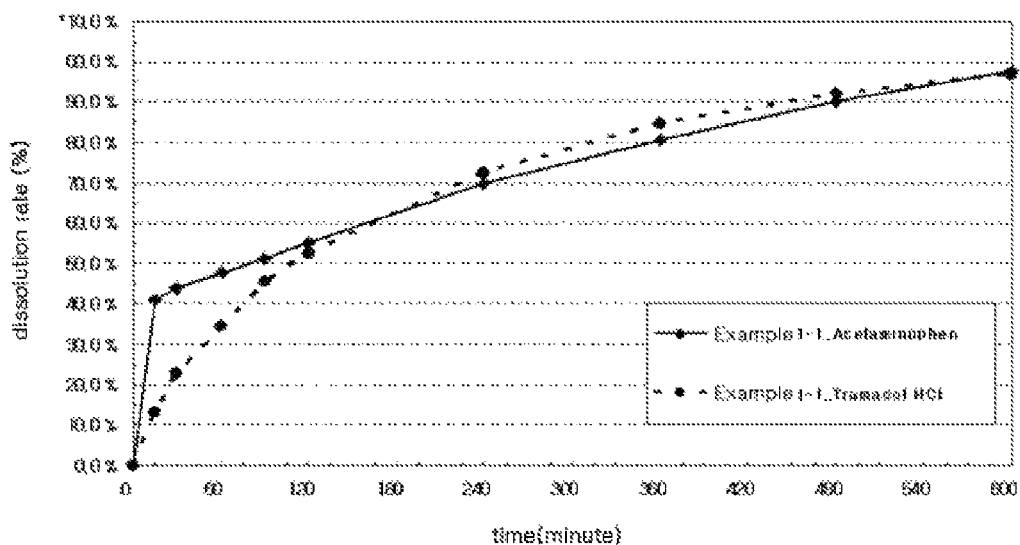
FIG. 1 shows dissolution rate of the pharmaceutical composition of the present invention with the composition of <Example 1-1> in water over time.

In order to achieve the above object, the present invention provide a pharmaceutical composition comprising a sustained-release part coated with water-insoluble polymer on the surface, comprising a first active pharmaceutical ingredient, at least one release control base selected from the group consisting of water-insoluble polymer, and water-soluble viscous polymer, and a pharmaceutically acceptable carrier; and, an immediate release part comprising a second active pharmaceutical ingredient and a pharmaceutically acceptable carrier.

Hereinafter, the present invention will be explained in detail.

The pharmaceutical composition of the present invention exhibits independent release properties of the immediate release part and the sustained-release part by coating the surface of the sustained-release part comprising an active pharmaceutical ingredient, a release control base and a pharmaceutically acceptable carrier with water-insoluble polymer to separate it from the immediate release part, it may be prepared by a relatively simple process without specification limitation to the contents and the kinds of usable active pharmaceutical ingredients, and it exhibits independent release properties of the immediate release part and the sustained-release part without being affected by pH change.

The water-insoluble polymer may be those exhibiting a solubility of 0.0001 g/ml of less in an aqueous solvent at any pH, and preferably one or more selected from the group consisting of water-insoluble cellulose, water-insoluble cellulose derivatives, polymethacrylate, polyalkylacrylate, methacrylate-ethylacrylate based copolymer, and a combination thereof, but not limited thereto. The water-insoluble cellulose may be preferably alkyl cellulose, more preferably ethyl cellulose. The water-insoluble cellulose derivatives may be preferably one or more selected from the group consisting of cellulose acetate, acetate phthalate, hydroxypropylmethylcellulose phthalate, and a combination thereof.

The water-soluble viscous polymer may exhibit a solubility of 0.01 g/ml or more in an aqueous solvent at any pH, and absorbs an aqueous solvent in an aqueous solution of 10% w/v, 20° C. to exhibit viscosity change of 1 mPas or more, based on the dry state. More preferably, it may be one or more selected from the group consisting of hydroxylalkylcellulose, hydroxypropylalkylcellulose, polyalkyleneoxide, sodium alginate, povidone, natural or synthetic gums, polyvinylalcohol, carboxymethylcellulose sodium, and a combination thereof. Most preferably, it may be one or more selected from hydroxypropylmethylcellulose, hydroxyethylcellulose, or a combination thereof.

The pharmaceutical composition of the present invention comprises a sustained-release part coated with water-insoluble polymer on the surface and an immediate-release part.

In the pharmaceutical composition of the present invention, the sustained-release part and the immediate-release part are combined, and to exhibit independent release properties of the sustained-release part and the immediate-release part, the surface of the sustained-release part is coated with water-insoluble polymer to separate it from the immediate-release part.

To exhibit independent release properties of the sustained-release part and the immediate-release part, the surface of the sustained-release part may be additionally coated with water-soluble viscous polymer, and more preferably, it may be primarily coated with water-soluble viscous polymer and secondarily coated with water-insoluble polymer.

In the examples, the surface of the sustained-release part is 1) coated with water-insoluble polymer (<Example 9-1> to <Example 68>), 2) coated with water soluble viscous polymer and additionally coated with water-insoluble polymer (<Example 1-1> to <Example 8>), or 3) coated with water-insoluble polymer and then coated with water-soluble viscous polymer, and additionally coated with water-insoluble polymer (<Example 69>), and combined with an immediate-release part to prepare a pharmaceutical composition of the present invention.

The sustained-release part comprises a first active pharmaceutical ingredient, at least one release control base selected from the group consisting of water-insoluble polymer and water-soluble viscous polymer, and pharmaceutically acceptable carrier, and the immediate-release part comprises a second active pharmaceutical ingredient and a pharmaceutically acceptable carrier.

Particularly, the first active pharmaceutical ingredient, the release control base, and the pharmaceutically acceptable carrier in the sustained-release part may be preferably mixed, but not limited thereto.

And, to control release of the sustained-release part, at least one selected from the group consisting of water-insoluble polymer and water-soluble viscous polymer may be used, and to more precisely control the release, a hydrophilic delivery vector or a hydrophobic delivery vector may be additionally used.

The hydrophilic delivery vector may be selected from the group consisting of polyalkylene glycol, carboxyvinyl hydrophilic polymer, and a combination thereof, and more preferably, it may be polyethyleneglycol, carbormer (Carbopol™), calcium carboxymethyl cellulose, sodium carboxymethyl cellulose, etc. with a molecular weight of 400~6,000, but not limited thereto.

The hydrophobic delivery vector may be selected from the group consisting of fatty acid, fatty acid ester, fatty alcohol, fatty acid (mono-, di-, tri-)glyceride, waxes, hydrogenated castor oil, hydrogenated vegetable oil, and a combination thereof. The fatty alcohol may be cetostearyl alcohol, stearyl alcohol, lauryl alcohol, myristyl alcohol, etc., the fatty acid ester may be glyceryl monostearate, glycerol monoleate, acetylated monoglyceride, tristearin, tripalmitin, cetyl ester wax, glyceryl palmitostearate, glyceryl behenate (Compritol 888 ATO™), and the wax may be beeswax, carnauba wax, glycol wax, and castor wax.

The sustained-release part and the immediate-release part may be in the form of independent granules, and the granules may be mixed in the pharmaceutical composition of the present invention, but not limited thereto.

In the examples, the sustained-release composition comprising a active pharmaceutical ingredient, a release control based, and a pharmaceutically acceptable carrier is prepared in the form of granules using a binding solution commonly used in the preparation of a pharmaceutical composition, and the immediate-release composition comprising a active pharmaceutical ingredient and a pharmaceutically acceptable carrier is also prepared in the form of granules using a binding solution.

As explained, to prepare the pharmaceutical composition of the present invention, the sustained-release part and the immediate-release part are respectively prepared and combined without requiring a specific process, and a separate process for tableting or compression molding in the form of a matrix is not required, and thus the process is very simple.

Furthermore, the contents and the kinds of the active pharmaceutical ingredients used in the pharmaceutical composition of the present invention are not limited. In the pharmaceutical composition, the sustained-release part and the immediate-release part are combined with being separated from each other, and the active pharmaceutical ingredient is contained respectively in the sustained-release part and the immediate-release, and thus, the active pharmaceutical ingredient requiring a rapid-acting property and the active pharmaceutical ingredient requiring a long-acting property may be independently used without limitation.

And, when a active pharmaceutical ingredient is coated on a conventionally used core material, the amount of coating is limited, however, according to the pharmaceutical composition of the present invention, the content of the active pharmaceutical ingredient may be easily controlled by controlling the contents of the active pharmaceutical ingredient when preparing the sustained-release part and the immediate-release part, and the contents are not limited.

And, the release degree of the active pharmaceutical ingredient contained in the sustained-release part may be controlled by controlling the content of the release control base selected from the group consisting of water-insoluble polymer, water-soluble viscous polymer, and a combination thereof. And, the initial release amount and the sustained-release amount may be easily controlled by controlling the mixing ratio of the sustained-release part and the immediate-release part.

In the pharmaceutical composition of the present invention, the first active pharmaceutical ingredient in the sustained-release part may be a single or complex ingredient, and it may be one or more selected from the group consisting of acetaminophen, tramadol, Niacin, Pitavastatin, Rosuvastatin, Atorvastatin, Rebamipide, Metformin, Glimepiride, Pioglitazone, Sitagliptin, Voglibose, Levosulpiride, Mosapride, Trimebutine, Itopride, Cilostazol, Limaprost, Sarpogrelate, Nifedipine, Losartan, Valsartan, Telmisartan, Olmesartan, Candesartan, Benidipine, Carvedilol, Atenolol, Valaciclovir, Choline Alfoscerate, Acetyl-1-carnitine, Venlafaxine, Risperidone, Quetiapine, Gabapentin, Pregabalin, Levetiracetam, Rivastigmine, Aceclofenac, Eperisone, Bepotastine, Acyclovir, and a pharmaceutically acceptable salt thereof, but not limited thereto.

And, the second active pharmaceutical ingredient in the immediate-release part may be a single or complex ingredient, and it may be one or more selected from the group consisting of acetaminophen, tramadol, Niacin, Pitavastatin, Rosuvastatin, Atorvastatin, Rebamipide, Metformin, Glimepiride, Pioglitazone, Sitagliptin, Voglibose, Levosulpiride, Mosapride, Trimebutine, Itopride, Cilostazol, Limaprost, Sarpogrelate, Nifedipine, Losartan, Valsartan, Telmisartan, Olmesartan, Candesartan, Benidipine, Carvedilol, Atenolol, Valaciclovir, Choline Alfoscerate, Acetyl-1-carnitine, Venlafaxine, Risperidone, Quetiapine, Gabapentin, Pregabalin, Levetiracetam, Rivastigmine, Aceclofenac, Eperisone, Bepotastine, Acyclovir, and a pharmaceutically acceptable salt thereof, but not limited thereto.

The active pharmaceutical ingredient in the sustained-release part and the active pharmaceutical ingredient in the immediate-release part may be the same or different, and they may be easily selected by a person having ordinary knowledge in the art.

And, the active ingredients may be preferably composed with the composition described in the following Table 1, according to the use or purpose of the pharmaceutical composition, but not limited thereto.

TABLE 1

| | | Single ingredient (API) | | Complex ingredient (API) | | | A immediate-release + A sustained-release + B sustained-release |
|---|---|---|---|---|---|---|---|
| | | Sustained-release (SR) | Immediate release + sustained-release | A sustained-release + B immediate-release | | A sustained-release + B sustained-release | |
| Digestiveduct and metabolism | ulcer | | rebamipide | | | | |
| | diabetes | metformin | | metformin | glimepiride | metformin | voglibose |
| | | | | metformin | pioglitazone | | |
| | | | | metformin | sitagliptin | | |
| | | | voglibose | voglibose | glimepiride pioglitazone | | |
| | Stomach function | | levosulpiride mosapride trimebutine itopride | | | | |
| | Blood and hemopoietic organ | | cilostazol limaprost sarpogrelate | | | | |
| Cardiovascular system | CCB + ARB | nifedipine | | nifedipine | losartan | | |
| | | | | nifedipine | valsartan | | |
| | | | | nifedipine | telmisartan | | |
| | | | | nifedipine | olmesartan | | |
| | | | | nifedipine | candesartan | | |
| | | benidipine | | benidipine | losartan | | |
| | | | | benidipine | valsartan | | |
| | | | | benidipine | telmisartan | | |
| | | | | benidipine | olmesartan | | |
| | | | | benidipine | candesartan | | |

TABLE 1-continued

|  |  | Single ingredient (API) | | Complex ingredient (API) | | | |
|---|---|---|---|---|---|---|---|
|  |  | Sustained-release (SR) | Immediate release + sustained-release | A sustained-release + B immediate-release | | A sustained-release + B sustained-release | A immediate-release + A sustained-release + B sustained-release |
|  | β-blocking | carvedilol |  | carvedilol | losartan |  |  |
|  |  |  |  | carvedilol | valsartan |  |  |
|  |  |  |  | carvedilol | telmisartan |  |  |
|  |  |  |  | carvedilol | olmesartan |  |  |
|  |  |  |  | carvedilol | candesartan |  |  |
|  |  | atenolol |  | atenolol | losartan |  |  |
|  |  |  |  | atenolol | valsartan |  |  |
|  |  |  |  | atenolol | telmisartan |  |  |
|  |  |  |  | atenolol | olmesartan |  |  |
|  |  |  |  | atenolol | candesartan |  |  |
|  | SLRA |  | niacin |  |  |  |  |
|  |  |  |  | niacin | atorvastatin |  |  |
|  |  |  |  | niacin | rosuvastatin |  |  |
|  |  |  |  | niacin | pitavastatin |  |  |
|  | (Antivirus) Virals |  | aciclovir valaciclovir |  |  |  |  |
| Nervous system | Nootropics | choline alfoscerate acetyl-1-carnitine |  |  |  |  |  |
|  | SNRI |  | venlafaxine |  |  |  |  |
|  | Antipsychotics |  | risperidone quetiapine |  |  |  |  |
|  | Analgesics |  | acetaminophen |  |  | (Sustained-release + immediate-release) acetaminophen | (Sustains-release + immediate-release) tramadol | (Sustains-release + immediate-release) acetaminophen (Sustains-release) tramadol |
|  | Anti epileptics |  | gabapentin pregabalin levetiracetam |  |  |  |  |
|  | Anti alz |  | rivastigmine |  |  |  |  |
| musculo-skeletal system | Anti-rheumatics |  | aceclofenac |  |  |  |  |
|  | Muscle relaxants |  | eperisone |  |  |  |  |
|  | Respiratory system |  | bepotastine |  |  |  |  |
| diabetes + hyperlipidemia |  |  |  | metformin | rosuvastatin |  |  |

Figure 11:
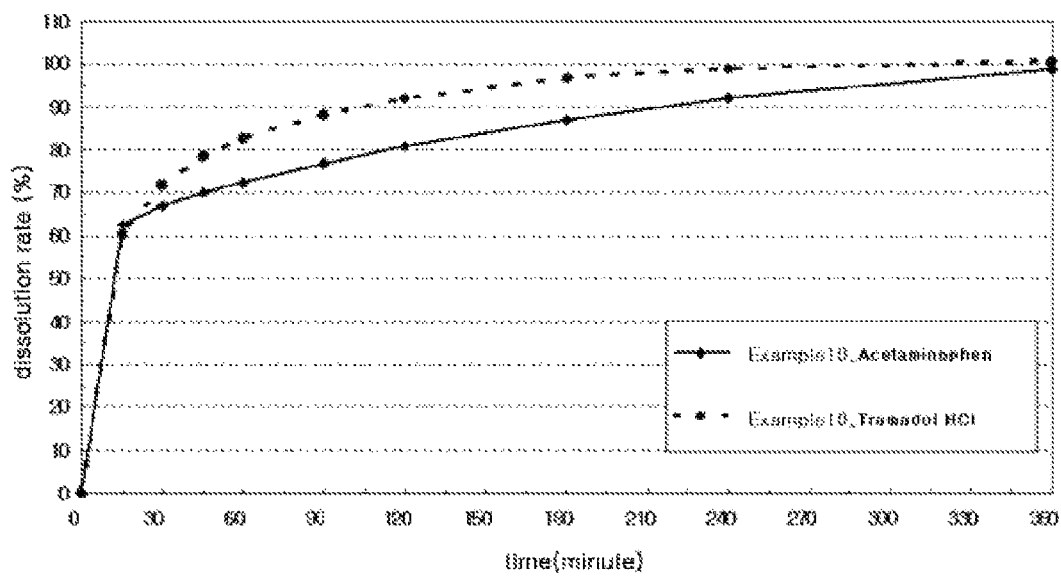
FIG. 11 shows dissolution rate of the pharmaceutical composition of the present invention with the composition of <Example 10> in water over time.
Figure 12:
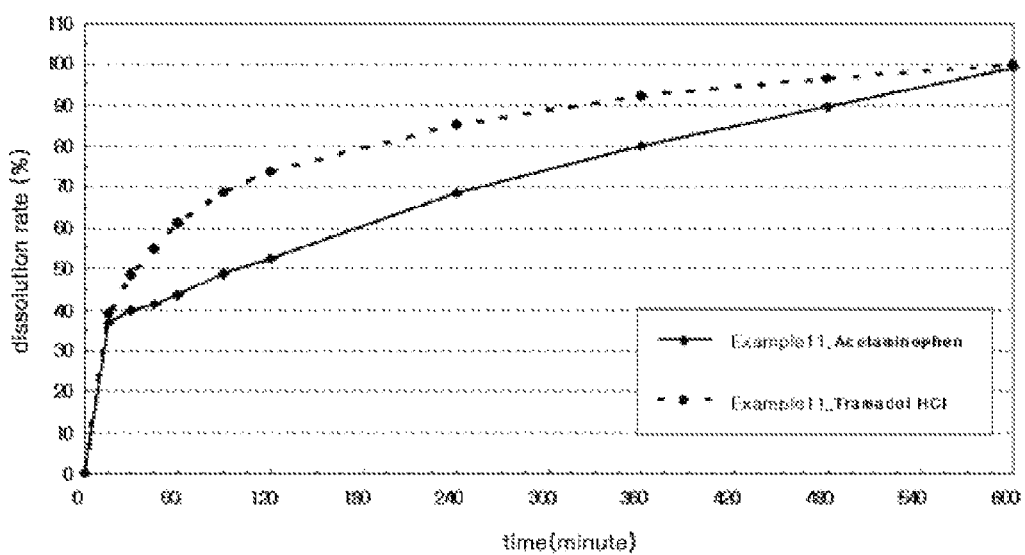
FIG. 12 shows dissolution rate of the pharmaceutical composition of the present invention with the composition of <Example 11> in water over time.

In the experimental examples of the present invention, acetaminophen or tramadol is used as a active pharmaceutical ingredient, the surface of the sustained-release part is coated with water-insoluble polymer or coated with water-soluble viscous polymer and additionally coated with water-insoluble polymer, and the release property of the prepared pharmaceutical composition is confirmed. As the result, it can be seen that the sustained-release part and the immediate-release part exhibit independent release properties (see acetaminophen in FIG. 1) without being affected by pH change (see FIG. 2), the release property may be controlled by the contents of the sustained-release part and the immediate-release part and the coating amount of the water-insoluble polymer (FIG. 7), the release property very similar to a representative conventional preparation Tylenol ER simultaneously having a rapid-acting property and a long-acting property (FIG. 10) is shown, and the initial release property of the active pharmaceutical ingredient may be smoothly controlled by controlling the compositional ratio of the sustained-release part and the immediate-release part (FIG. 11 to FIG. 12).

Figure 13:
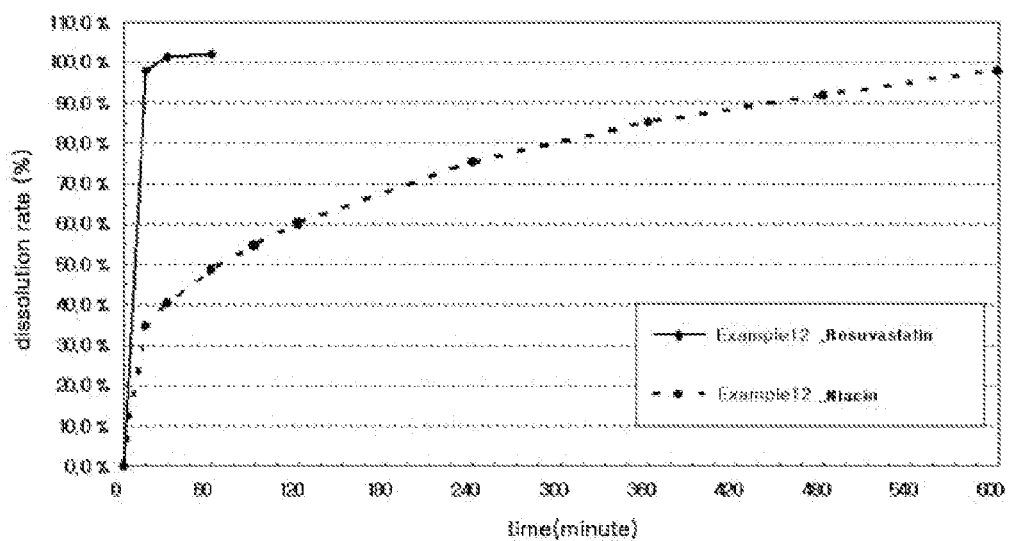
FIG. 13 shows dissolution rate of the pharmaceutical composition of the present invention with the composition of <Example 12> in water over time.
Figure 14:
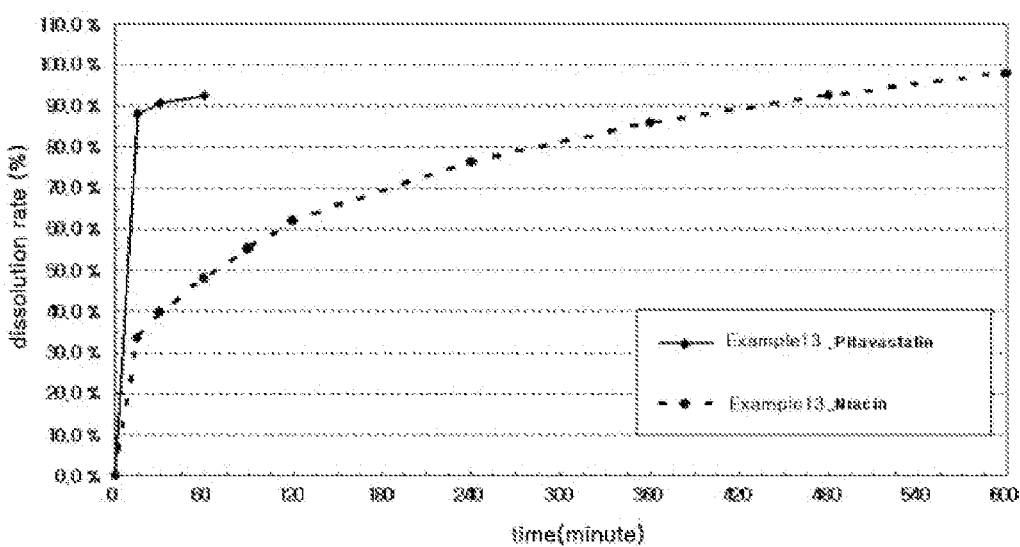
FIG. 14 shows dissolution rate of the pharmaceutical composition of the present invention with the composition of <Example 13> in water over time.
Figure 15:
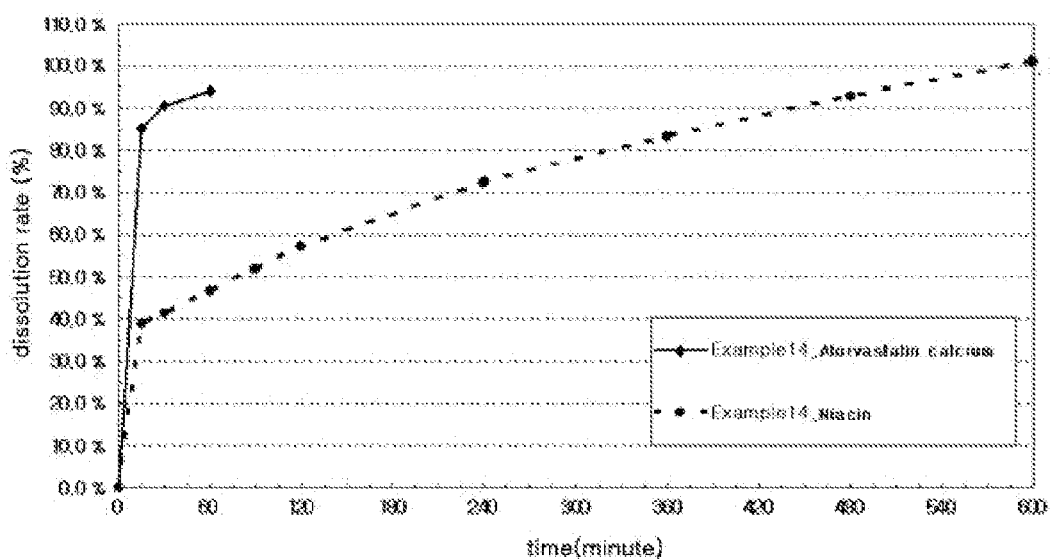
FIG. 15 shows dissolution rate of the pharmaceutical composition of the present invention with the composition of <Example 14> in water over time.

And, in the case of a pharmaceutical composition prepared by using rosuvastatin, pitavastatin, atorvastatin calcium or niacin and coating the surface of the sustained-release part with water-insoluble polymer, the sustained-release part and the immediate-release part exhibit independent release properties (FIG. 13 to FIG. 15).

Figure 16:
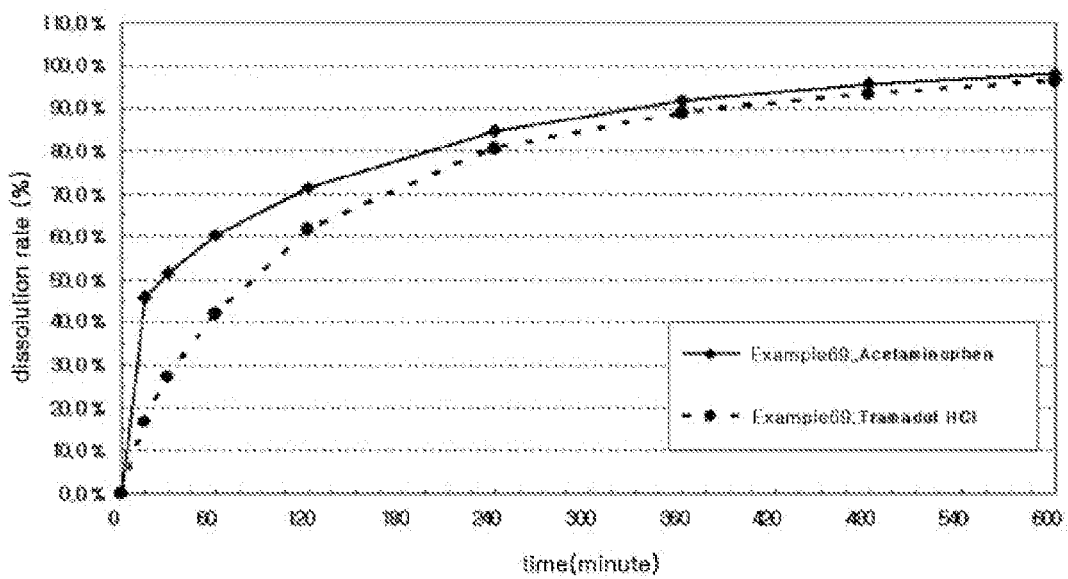
FIG. 16 shows dissolution rate of the pharmaceutical composition of the present invention with the composition of <Example 69> at pH 6.8 over time.

And, in the case of a pharmaceutical composition prepared by using various active ingredients described in the above Table 1 as well as the rosuvastatin, pitavastatin, atorvastatin calcium or niacin, the sustained-release part and the immediate-release part exhibit independent release properties, indicating that the kinds of the active pharmaceutical ingredient are not limited (Table 7 and Table 8, FIG. 16).

The dosage form the pharmaceutical composition of the present invention may be preferably a tablet, but not limited thereto. The pharmaceutical composition may be prepared in the form of a tablet by combining a pharmaceutically acceptable carrier with the sustained-release part and the immediate-release part and tableting, and the tablet may be prepared by a relatively simple process without requiring a special tableting machine.

The pharmaceutically acceptable carrier may be preferably selected from excipient, a disintegrating agent, a lubricant, or a combination thereof, and the excipient, disintegrating agent, lubricant may be easily selected by a person having ordinary knowledge in the art. More preferably, the excipient may include hydroxypropylcellulose, cellactose, kollidon, silicified microcrystalline cellulos, and a combination thereof, the disintegrating agent may include sodium croscarmellose, and the lubricant may include magnesium stearate.

According to the pharmaceutical composition of the present invention, the sustained-release part and the immediate-release part may exhibit independent release properties by coating the surface of the sustained-release part comprising a active pharmaceutical ingredient, a release control base and a pharmaceutically acceptable carrier with water-insoluble polymer so as to separate it from the immediate-release part, the initial release property of the active pharmaceutical ingredient may be smoothly controlled by controlling the compositional ratio of the immediate-release part and the sustained-release part, and it may be prepared by a relatively simple process without limitation to the contents and the kinds of usable active pharmaceutical ingredients.

Hereinafter, the present invention will be explained in detail by the following Examples.

However, these examples are only to illustrate the present invention, and the scope of the present invention is not limited thereto.

EXAMPLE

Preparation of a Pharmaceutical Composition Simultaneously Having Rapid-Acting Property and Long-Acting Property 1) Preparation of a Sustained-Release Part Having Long-Acting Property According to <Example 1-1> to <Example 8> described in the following Tables 2 and 3, a binding solution was sprayed to a mixture of active pharmaceutical ingredients, a release control base and a pharmaceutically acceptable carrier to prepare sustained-release granules, and a spray solution of water-soluble viscous polymer (5% w/w, mixing ethanol and water at 8:2) was sprayed to the prepared granules to primarily coat them, and then, a spray solution of water-insoluble polymer (6% w/w, mixing ethanol and water at 9:1) was sprayed thereto to secondarily coat them, thereby preparing a sustained-release part having long-acting property.

And, according to <Example 9-1> to <Example 68> described in the following Table 3 to Table 5-2, a binding solution was sprayed to a mixture of active pharmaceutical ingredients, a release control base and a pharmaceutically acceptable carrier to prepare sustained-release granules, and a spray solution of water-insoluble polymer (6% w/w, mixing ethanol and water at 9:1) was sprayed to the prepared granules to coat them, thereby preparing a sustained-release part having long-acting property.

Additionally, according to <Example 69> described in the following Table 6, a binding solution was sprayed to a mixture of active pharmaceutical ingredients, a release control base and a pharmaceutically acceptable carrier to prepare sustained-release granules, and a spray solution of water-insoluble polymer (6% w/w, mixing ethanol and water at 9:1) was sprayed to the prepared granules to primarily coat them, and then, a spray solution of water-soluble viscous polymer (5% w/w, mixing ethanol and water at 8:2) was sprayed thereto to secondarily coat them, and a spray solution of water-insoluble polymer (6% w/w, mixing ethanol and water at 9:1) to tertiary coat them, thereby preparing a sustained-release part having long-acting property.

Specifically, acetaminophen and tramadol HCl were used as release drugs in <Example 1-1> to <Example 11> and <Example 69>, and the active ingredients of the sustained-release part described in Table 5-1 were used as release drugs in <Example 15> to <Example 68>, and at least one selected from colloidal silicon dioxide, methactylate-ethylacrylate based copolymer (Registered trademark: Eudragit), hydroxypropylcellulose, hydroxyethylcellulose, calcium carbonate, sodium lauryl sulfate, hydroxypropylmethylcellulose, microcrystalline cellulose, pregelatinized starch, polyethyleneoxide, croscarmellose sodium, and ethylcellulose were mixed therewith, and then, a binding solution was sprayed to prepare sustained-release granules.

Water-soluble viscous polymer was sprayed to the prepared sustained-release granules to primarily coat them, and water-insoluble polymer was sprayed to the primarily coated sustained-release granules to secondarily coat them (<Example 1-1> to <Example 8>).

Alternatively, only water-insoluble polymer was sprayed to the prepared sustained-release granules to coat them (<Example 9-1> to <Example 11>, and <Example 15> to <Example 68>).

Alternatively, water-insoluble polymer was sprayed to the prepared sustained-release granules to primarily coat them, water-soluble viscous polymer was sprayed to the primarily coated sustained-release granules to secondarily coat them, and then, water-insoluble polymer was additionally sprayed to the secondarily coated sustained-release granules to tertiary coat them (<Example 69>).

As the water-soluble viscous polymer, at least one selected from hydroxypropylcellulose, hydroxypropylmethylcellulose, hydroxyethylcellulose, and polyethyleneoxide was used. As the water-insoluble polymer, at least one selected from ethylcellulose, methacrylate-ethylacrylate based copolymer (Registered trademark: Eudragit), and microcrystalline cellulose was used.

Meanwhile, according to <Example 12> to <Example 14> described in the following Table 4, a binding solution was sprayed to a sustained-release mixture to prepare sustained-release granules, and water-insoluble polymer was sprayed to the prepared granules to coat them, thereby preparing a sustained-release part having long-acting property.

Specifically, in <Example 12> to <Example 14>, Niacin was used as release drug, and methacrylate-ethylacrylate based copolymer (Registered trademark: Eudragit) and hydroxyethylcellulose were mixed therewith, and then, a binding solution was sprayed thereto to prepare sustained-release granules, and then, water-insoluble polymer ethylcellulose was sprayed to the sustained-release granules to coat them.

2) Preparation of an Immediate-Release Part Having Rapid-Acting Property

According to <Example 1-1> to <Example 14> described in the following Tables 2 to 4, and <Example 15> to <Example 69> described in the following Tables 5-1 to 6, a binding solution was sprayed to an immediate-release mixture to prepare immediate-release granules.

Specifically, acetaminophen was used as release drug in <Example 1-1> to <Example 9-3> and <Example 69> described in the following Tables 2, 3 and 6, and acetaminophene and tramadol were used as release drugs in <Example 10> and <Example 11> described in Table 3, and at least one selected from lactose, croscarmellose sodium, colloidal silicon dioxide, hydroxypropylcellulose, microcrystalline cellulose, pregelatinized starch, low-substituted hydroxypropylcellulose, and powdered cellulose were mixed therewith, and then, a binding solution was sprayed thereto to prepare immediate-release granules.

Meanwhile, in <Example 12> to <Example 14> described in the following Table 4 and <Example 15> to <Example 68> described in the following Tables 5-1 and 5-2, the active ingredients of the immediate-release part were used as release drugs, and a binding solution was sprayed to the immediate-release mixture to prepare immediate-release granules.

Specifically, in <Example 12> to <Example 14> and <Example 15> to <Example 68>, the active ingredients of the immediate-release part described in Table 4 and Table 5-1 were used as release drugs, and at least one selected from colloidal silicon dioxide, microcrystalline cellulose, hydroxypropylcellulose, calcium carbonate, magnesium aluminometasilicate, and tribasic calcium phosphate were mixed therewith, and then, a binding solution was sprayed to prepare immediate-release granules.

3) Preparation of Pharmaceutical Composition Simultaneously Having Rapid-Acting Property and Long-Acting Property 3-1) Example 12 to 14, 17 to 19, 22, 23, 32 to 36, 38 to 42, 44 to 48, 50 to 54, 68

The compositions were prepared substantially by the same method as the above 1) and 2), except that a sustained-release part was prepared using the first active pharmaceutical ingredient and an immediate-release part was prepared using the second active pharmaceutical ingredient of the complex active ingredients as described in Table 4, Table 5-1 and Table 5-2, and excipient and a disintegrating agent were added to the prepared sustained-release part and the immediate-release part, and a lubricant was additionally added thereto, and then, the mixture was tableted to prepare a tablet with a hardness of 12~20 kp. Specifically, hydroxypropylcellulose was used as the excipient, croscarmellose sodium was used as the disintegrating agent, and magnesium stearate was used as the lubricant.

3-2) Example 16, 21, 31, 37, 43, 49, 56, 57

The compositions were prepared substantially by the same method as the above 1), except that only a sustained-release part was prepared using a single active ingredient as described in the following Tables 5-1 and 5-2, excipient and a disintegrating agent were added to the prepared sustained-release part and a lubricant was additionally added thereto, and then, the mixture was tableted to prepare a tablet with a hardness of 12~20 kp. Specifically, hydroxypropylcellulose was used as the excipient, croscarmellose sodium was used as the disintegrating agent, and magnesium stearate was used as the lubricant.

3-3) Example 15, 24 to 30, 55, 58 to 67

The compositions were prepared substantially by the same method as the above 1) and 2), except that a sustained-release part and an immediate-release part were prepared using a single active ingredient as described in the following Tables 5-1 and 5-2, excipient and a disintegrating agent were added to the prepared sustained-release part and immediate-release part and a lubricant was additionally added, and then, the mixture was tableted to prepared a table with a hardness of 12~20 kp. Specifically, hydroxypropylcellulose was used as the excipient, croscarmellose sodium was used as the disintegrating agent, and magnesium stearate was used as the lubricant.

3-4) Example 20

The composition was prepared substantially by the same method as the above 1), except that only a sustained-release part was prepared using complex active ingredient as described in Tables 5-1 and 5-2, excipient and a disintegrating agent were added to the prepared sustained-release part and a lubricant was additionally added, and then, the mixture was tableted to prepared a table with a hardness of 12~20 kp. Specifically, hydroxypropylcellulose was used as the excipient, croscarmellose sodium was used as the disintegrating agent, and magnesium stearate was used as the lubricant.

3-5) Example 1-1 to 9-3, 69

The compositions were prepared substantially by the same method as the above 1) and 2), except that only a sustained-release part was prepared using a first active pharmaceutical ingredient (tramadol HCl) and a sustained-release part and an immediate-release part were prepared using a second active pharmaceutical ingredient (acetaminophen) as described in Tables 2, 3 and 6, and excipient and a disintegrating agent were added to the prepared sustained-release part and a lubricant was additionally added, and then, the mixture was tableted to prepare a tablet with hardness of 12~20 kp. Specifically, hydroxypropylcellulose was used as the excipient, croscarmellose sodium was used as the disintegrating agent, and magnesium stearate was used as the lubricant.

3-6) Example 10 and 11

The compositions were prepared substantially by the same method as the above 1) and 2), except that a sustained-release part and an immediate-release part were prepared using a first active pharmaceutical ingredient (tramadol HCl) and a sustained-release part and an immediate-release part were prepared using a second active pharmaceutical ingredient (acetaminophen), and excipient and a disintegrating agent were added to the prepared sustained-release part and a lubricant was additionally added, and then, the mixture was tableted to prepare a tablet with hardness of 12~20 kp. Specifically, hydroxypropylcellulose was used as the excipient, croscarmellose sodium was used as the disintegrating agent, and magnesium stearate was used as the lubricant.

TABLE 2

Compositions-I of the pharmaceutical compositions simultaneously having rapid-acting property and long-acting property

| | | | Ingredient | Example 1-1 | Example 1-2 | Example 2 | Example 3 | Example 4 | Example 5 | Example 6 |
|---|---|---|---|---|---|---|---|---|---|---|
| SUSTAINED RELEASE PART | GRANULES | Mixture | Acetaminophen | 26.0% | 24.4% | 31.2% | 28.9% | 26.0% | 31.2% | 26.0% |
| | | | Tramadol HCl | 5.0% | 4.7% | 6.0% | 5.6% | 5.0% | 6.0% | 5.0% |
| | | | Colloidal Silicon Dioxide | 0.05% | 0.04% | 0.04% | 0.04% | 0.07% | 0.09% | 0.05% |
| | | | Eudragit | 3.3% | 6.3% | 4.7% | 4.3% | | 3.3% | 5.0% |

TABLE 2-continued

Compositions-I of the pharmaceutical compositions simultaneously having rapid-acting property and long-acting property

| | | | Ingredient | Example 1-1 | Example 1-2 | Example 2 | Example 3 | Example 4 | Example 5 | Example 6 |
|---|---|---|---|---|---|---|---|---|---|---|
| | | | Hydroxyethylcellulose | 3.3% | 6.3% | | | | 3.3% | |
| | | | Calcium carbonate | 1.1% | 1.1% | 1.3% | 1.2% | | | |
| | | | Sodium Lauryl Sulfate | 0.5% | 0.4% | 0.6% | 0.6% | | 0.2% | 0.2% |
| | | | Hydroxypropylmethylcellulose | | | | | | | 2.8% |
| | | | Microcrystalline cellulose | | | | | 6.7% | | |
| | | | Hydroxypropylcellulose | | | | | 6.7% | | |
| | | Binding solution | Hydroxypropylcellulose | 0.7% | 0.6% | 0.4% | 0.4% | 0.6% | 0.5% | 0.3% |
| | | | Water | 2.5% | 2.1% | 1.4% | 1.4% | 2.1% | 1.8% | 1.1% |
| | | | Ethanol | 2.5% | 2.1% | 1.4% | 1.4% | 2.1% | 1.8% | 1.1% |
| | | First spray | Hydroxypropylmethylcellulose | 0.3% | 1.3% | | | | 0.5% | 0.9% |
| | | | Hydroxyethylcellulose | 2.5% | 2.6% | 2.5% | 2.4% | 0.5% | | |
| | | | Talc | 1.0% | 0.6% | 0.4% | 0.5% | 0.1% | | 0.3% |
| | | Second Spray | Triethylcitrate | 1.7% | 1.2% | 1.5% | 1.2% | | | 3.1% |
| | | | Poylethyleneglycol | 0.6% | 1.2% | | 1.2% | | | |
| | | | Triacetin | | | | | 0.4% | 0.3% | |
| | | | Talc | 1.7% | 4.0% | 1.5% | 2.3% | 0.8% | | 3.1% |
| | | | Eudragit | | | | | 4.6% | 4.5% | |
| | | | Ethyl Cellulose | 11.4% | 13.2% | 9.9% | 11.7% | 7.6% | 7.5% | primary: 6.15% secondary: 12.30% |
| IMMEDIATE RELEASE PART | GRANULES | Mixture | Acetaminophen | 17.3% | 16.3% | 20.8% | 19.3% | 17.3% | 20.8% | 17.3% |
| | | | Tramadol HCl | | | | | | | |
| | | | Lactose | 3.7% | 3.4% | 4.3% | 4.1% | 3.7% | 4.4% | 3.7% |
| | | | Croscarmellose sodium | 0.7% | 0.6% | 0.8% | 0.7% | 0.7% | 0.8% | 0.7% |
| | | | Colloidal Silicon Dioxide | 0.02% | 0.02% | 0.02% | 0.02% | 0.02% | 0.02% | 0.02% |
| | | Binding solution | Hydroxypropylcellulose | 0.6% | 0.6% | 0.8% | 0.7% | 0.7% | 0.8% | 0.7% |
| | | | Water | 2.1% | 2.1% | 2.8% | 2.5% | 2.5% | 2.8% | 2.5% |
| | | | Ethanol | 2.1% | 2.1% | 2.8% | 2.5% | 2.5% | 2.8% | 2.5% |
| | | Additional Excipients | Silicified Microcrystalline cellulose | 10.6% | 5.7% | 7.0% | 8.6% | 10.6% | 8.1% | primary: 18.35% secondary: 12.20% |
| | | | Hydroxypropylcellulose | 5.1% | 2.5% | 3.5% | 3.4% | 5.1% | 5.0% | 3.5% |
| | | | Croscarmellose sodium | 2.3% | 2.4% | 2.2% | 2.3% | 2.3% | 2.2% | 2.3% |
| | | | Magnesium Stearate | 0.5% | 0.5% | 0.5% | 0.5% | 0.5% | 0.5% | 0.5% |
| | | | | 100.0% | 100.0% | 100.0% | 100.0% | 100.0% | 100.0% | 100.0% |

TABLE 3

Compositions-II of the pharmaceutical compositions simultaneously having rapid-acting property and long-acting property

| | | | Ingredient | Example 7 | Example 8 | Example 9-1 | Example 9-2 | Example 9-3 | Example 10 | Example 11 |
|---|---|---|---|---|---|---|---|---|---|---|
| SUSTAINED RELEASE PART | GRANULES | Mixture | Acetaminophen | 33.9% | 32.5% | | 30.8% | 30.8% | 30.8% | 20.8% | 31.2% |
| | | | Tramadol HCl | 6.5% | | 6.2% | | | | 2.4% | 3.6% |
| | | | Colloidal Silicon Dioxide | 0.05% | 0.05% | | 0.05% | 0.05% | 0.05% | 0.05% | 0.05% |
| | | | Eudragit | 3.6% | | 0.5% | | 5.4% | 3.6% | 5.7% | 8.5% |
| | | | Ethyl Cellulose | | | | 3.6% | | | | |
| | | | Hydroxyethylcellulose | 3.6% | | 0.5% | | | | | |
| | | | Microcrystalline cellulose | | 3.8% | | | | | | |
| | | | polyethyleneoxide | | | | 1.8% | | 1.8% | 0.3% | 0.5% |
| | | Binding solution | Pregelatinied starch | | 1.9% | | | | | | |
| | | | Ethyl Cellulose | 0.5% | | 0.1% | 0.5% | 0.6% | 0.5% | 0.5% | 0.8% |
| | | | Water | 1.8% | 6.7% | 0.4% | 1.8% | 2.1% | 1.8% | 1.8% | 2.8% |
| | | | Ethanol | 1.8% | 6.7% | 0.4% | 1.8% | 2.1% | 1.8% | 1.8% | 2.8% |
| | First spray | | Hydroxyethylcellulose | 0.5% | 0.5% | | | | | | |

TABLE 3-continued

Compositions-II of the pharmaceutical compositions simultaneously having rapid-acting property and long-acting property

|  |  | Ingredient | Example 7 | Example 8 | Example 9-1 | Example 9-2 | Example 9-3 | Example 10 | Example 11 |
|---|---|---|---|---|---|---|---|---|---|
| IMMEDIATE RELEASE PART | Second spray | Triacetin | 0.8% | 0.4% |  |  |  | 0.4% | 0.7% |
|  |  | Eudragit | 4.8% | 4.6% |  |  |  |  |  |
|  |  | Ethyl Cellulose | 8.0% | 7.6% | 5.3% | 5.5% | 5.5% | 4.4% | 6.7% |
|  | GRANULES Mixture | Acetaminophen | 22.6% | 21.7% | 37.6% | 37.6% | 37.6% | 31.2% | 20.8% |
|  |  | Tramadol HCl |  |  |  |  |  | 3.6% | 2.4% |
|  |  | Colloidal Silicon Dioxide | 0.05% | 0.03% | 0.03% | 0.03% | 0.03% | 0.03% | 0.03% |
|  |  | Low-substituted Hydroxypropyl Cellulose | 4.5% |  |  |  |  |  |  |
|  |  | Microcrystalline cellulose |  | 2.5% | 3.7% | 3.7% | 3.7% | 9.6% | 5.8% |
|  | Binding solution | Pregelatinied starch | 3.9% | 1.3% | 1.9% | 1.9% | 1.9% | 1.3% | 1.3% |
|  |  | Water | 13.7% | 4.6% | 6.7% | 6.7% | 6.7% | 4.6% | 4.6% |
|  |  | Ethanol | 13.7% | 4.6% | 6.7% | 6.7% | 6.7% | 4.6% | 4.6% |
|  | Additional Excipients | Silicified Microcrystalline cellulose |  |  | 7.2% | 7.8% | 7.8% | 10.6% | 9.3% |
|  |  | Kollidon |  |  | 4.2% | 3.3% | 3.4% | 5.6% | 4.8% |
|  |  | Cellactose | 4.3% | 12.3% |  |  |  |  |  |
|  |  | Croscarmellose sodium | 1.9% | 3.0% | 2.8% | 2.8% | 2.8% | 3.0% | 3.0% |
|  |  | Magnesium Stearate | 0.5% | 0.5% | 0.5% | 0.5% | 0.5% | 0.5% | 0.5% |
|  |  |  |  | 100.0% | 100.0% | 100.0% | 100.0% | 100.0% | 100.0% |

TABLE 4

Compositions-III of the pharmaceutical compositions simultaneously having rapid-acting property and long-acting property

|  |  | Ingredient | Example 12 | Example 13 | Example 14 |
|---|---|---|---|---|---|
| SUSTAINED RELEASE PART | GRANULES Mixture | Niacin | 33.3% | 33.3% | 33.3% |
|  |  | Eudragit | 10.3% | 10.3% | 10.3% |
|  |  | Hydroxyethylcellulose | 2.8% | 2.8% | 2.8% |
|  | Binding Solution | Hydroxypropylcellulose | 1.0% | 1.0% | 1.0% |
|  |  | water | 2.8% | 2.8% | 2.8% |
|  |  | ethanol | 2.8% | 2.8% | 2.8% |
|  | First spray | Triethylcitrate | 1.0% | 1.0% | 1.0% |
|  |  | Talc | 1.0% | 1.0% | 1.0% |
|  |  | Ethyl Cellulose | 10.4% | 10.4% | 10.4% |
| IMMEDIATE RELEASE PART | GRANULES mixture | Rosuvastatin | 0.3% |  |  |
|  |  | Pitavastatin |  | 0.1% |  |
|  |  | Atorvastatin calcium |  |  | 0.6% |
|  |  | Niacin | 22.2% | 22.2% | 22.2% |
|  |  | Tribasic Calcium Phosphate | 1.4% |  |  |
|  |  | Magnesium Aluminometasilicate |  | 1.4% |  |
|  |  | Calcium carbonate |  |  | 1.4% |
|  |  | Colloidal Silicon Dioxide | 0.1% | 0.1% | 0.1% |
|  |  | Microcrystalline cellulose | 3.3% | 3.3% | 3.3% |
|  | Binding solution | Hydroxypropylcellulose | 0.8% | 0.8% | 0.8% |
|  |  | water | 2.8% | 2.8% | 2.8% |
|  |  | Ethanol | 2.8% | 2.8% | 2.8% |
|  | Additional Excipients | Kollidon | 4.0% | 4.0% | 4.0% |
|  |  | Silicified Microcrystalline cellulose | 5.1% | 5.3% | 4.8% |
|  |  | Croscarmellose sodium | 2.5% | 2.5% | 2.5% |
|  |  | Magnesium Stearate | 0.5% | 0.5% | 0.5% |
|  |  |  | 100.0% | 100.0% | 100.0% |

TABLE 5-1

Compositions-IV of the pharmaceutical compositions simultaneously having rapid-acting property and long-acting property

| | | Sustained-release part Granules | | | | | | | |
|---|---|---|---|---|---|---|---|---|---|
| | | Mixture | | | | | Binding solution | | |
| Ingredient | Active ingredient | Colloidal Silicon Dioxide | Eudragit | Hydroxy ethyl cellulose | Microcrystalline cellulose | Croscarmellose sodium | Hydroxy propyl cellulose | water | ethanol |
| Example 15 | Rebamipide 17.8% | 0.1% | 3.6% | 3.6% | 3.6% | 0.3% | 0.6% | 10% solid cont. | |
| Example 16 | Metformin HCl 53.0% | 0.1% | 5.30% | 5.3% | 5.3% | 0.7% | 1.4% | 10% solid cont. | |
| Example 17 | Metformin HCl 53.1% | 0.1% | 5.26% | 5.3% | 5.3% | 0.7% | 1.4% | 10% solid cont. | |
| Example 18 | Metformin HCl 53.0% | 0.1% | 5.02% | 5.0% | 5.0% | 0.7% | 1.3% | 10% solid cont. | |
| Example 19 | Metformin HCl 53.0% | 0.1% | 4.74% | 4.7% | 4.7% | 0.6% | 1.2% | 10% solid cont. | |
| Example 20 | Metformin HCl 52.9% Voglibose 0.05% | 0.1% | 5.29% | 5.29% | 5.29% | 0.69% | 1.39% | 10% solid cont. | |
| Example 21 | Voglibose 0.8% | | 1.88% | 1.9% | 5.6% | 1.9% | 0.2% | 10% solid cont. | |
| Example 22 | Voglibose 0.8% | | 1.81% | 1.8% | 5.4% | 1.8% | 0.2% | 10% solid cont. | |
| Example 23 | Voglibose 0.6% | | 1.41% | 1.4% | 4.2% | 1.4% | 0.2% | 10% solid cont. | |
| Example 24 | Levosulpiride 28.2% | | 5.64% | 5.6% | 5.6% | 0.5% | 0.9% | 10% solid cont. | |
| Example 25 | Mosapride citrate 24.2% | | 4.85% | 4.8% | 4.8% | 0.4% | 0.8% | 10% solid cont. | |
| Example 26 | Trimebutine maleate 32.9% | | 6.58% | 6.6% | 6.6% | 0.5% | 1.1% | 10% solid cont. | |
| Example 27 | Itopride HCl 32.9% | | 6.57% | 6.6% | 6.6% | 0.5% | 1.1% | 10% solid cont. | |
| Example 28 | Cilostazol 32.3% | | 6.46% | | 6.5% | 0.5% | 0.9% | 10% solid cont. | |
| Example 29 | Limaprost Alpha-Cyclodextrin Clathrate 0.6% | | 12.45% | 12.5% | 12.5% | 0.4% | 2.0% | 10% solid cont. | |
| Example 30 | Sarpogrelate HCl 32.9% | 0.1% | 6.57% | 6.6% | 6.6% | 0.5% | 1.1% | 10% solid cont. | |
| Example 31 | Nifedipine 51.7% | | 10.34% | | 6.9% | 0.7% | 1.4% | 10% solid cont. | |

| | | Immediate-release part | | | | | | | |
|---|---|---|---|---|---|---|---|---|---|
| | | Granules | | | | | Additional Excipients | | |
| | | Mixture | | Binding solutioon | | | | | |
| Ingredient | Active ingredient | Microcrystalline cellulose | Colloidal Silicon Dioxide | Hydroxy propyl cellulose | water | ethanol | Hydroxy propyl cellulose | Croscarmellose sodium | Magnesium Stearate |
| Example 15 | Rebamipide 26.6% | 26.6% | 0.1% | 0.7% | 10% solid cont. | | 4.2% | 2.1% | 0.6% |
| Example 16 | | | | | | | 3.6% | 1.8% | 0.5% |
| Example 17 | Glimepiride 0.2% | | | | | | 3.6% | 1.8% | 0.5% |
| Example 18 | Pioglitazone HCl 1.7% | | | | | | 3.6% | 1.8% | 0.5% |

TABLE 5-1-continued

Compositions-IV of the pharmaceutical compositions simultaneously having rapid-acting property and long-acting property

| | | | | | | | | |
|---|---|---|---|---|---|---|---|---|
| Example 19 | Sitagliptin phosphate monohydrate 4.7% | 4.7% | 0.0% | 0.2% | 10% solid cont. | 3.7% | 1.8% | 0.5% |
| Example 20 | | | | | | 3.6% | 1.8% | 0.5% |
| Example 21 | | 76.3% | | | | 4.4% | 2.2% | 0.7% |
| Example 22 | Glimepiride 3.6% | 73.3% | | | | 4.4% | 2.2% | 0.7% |
| Example 23 | Pioglitazone HCl 23.2% | 57.1% | | | | 4.5% | 2.2% | 0.7% |
| Example 24 | Levosulpiride 14.1% | 16.9% | 0.3% | 0.6% | 10% solid cont. | 3.9% | 2.0% | 0.6% |
| Example 25 | Mosapride citrate 8.1% | 32.3% | | | | 4.0% | 2.0% | 0.6% |
| Example 26 | Trimebutine maleate 16.4% | 4.9% | 0.1% | 0.4% | 10% solid cont. | 3.8% | 1.9% | 0.6% |
| Example 27 | Itopride HCl 16.4% | 4.9% | 0.2% | 0.4% | 10% solid cont. | 3.8% | 1.9% | 0.6% |
| Example 28 | Cilostazol 23.9% | 7.2% | 0.1% | 0.6% | 10% solid cont. | 3.9% | 2.0% | 0.6% |
| Example 29 | Limaprost Alpha-Cyclodextrin Clathrate 0.3% | 30.8% | | | | 9.3% | 4.7% | 1.4% |
| Example 30 | Sarpogrelate HCl 16.4% | 4.9% | 0.1% | 0.4% | 10% solid cont. | 3.8% | 1.9% | 0.6% |
| Example 31 | | | | | | 3.6% | 1.8% | 0.5% |

| | Sustained-release part Granules | | | | | | | |
|---|---|---|---|---|---|---|---|---|
| | Mixture | | | | | | Binding solution | |
| Ingredient | Active ingredient | Colloidal Silicon Dioxide | Eudragit | Hydroxy ethyl cellulose | Microcrystalline cellulose | Croscarmellose sodium | Hydroxy propyl cellulose | water ethanol |
| Example 32 | Nifedipine 23.0% | | 4.60% | | 3.1% | 0.3% | 0.6% | 10% solid cont. |
| Example 33 | Nifedipine 17.3% | | 3.46% | | 2.3% | 0.2% | 0.5% | 10% solid cont. |
| Example 34 | Nifedipine 25.9% | | 5.17% | | 3.4% | 0.3% | 0.7% | 10% solid cont. |
| Example 35 | Nifedipine 26.4% | | 5.27% | | 3.5% | 0.4% | 0.7% | 10% solid cont. |
| Example 36 | Nifedipine 20.8% | | 4.16% | | 2.8% | 0.3% | 0.6% | 10% solid cont. |
| Example 37 | Benidipine HCl 43.1% | | 8.62% | 8.6% | 8.6% | 0.7% | 1.4% | 10% solid cont. |
| Example 38 | Benidipine HCl 4.9% | | 0.98% | 1.0% | 1.0% | 0.1% | 0.2% | 10% solid cont. |
| Example 39 | Benidipine HCl 3.2% | | 0.64% | 0.6% | 0.6% | 0.1% | 0.1% | 10% solid cont. |
| Example 40 | Benidipine HCl 5.9% | | 1.19% | 1.2% | 1.2% | 0.1% | 0.2% | 10% solid cont. |
| Example 41 | Benidipine HCl 6.2% | | 1.23% | 1.2% | 1.2% | 0.1% | 0.2% | 10% solid cont. |
| Example 42 | Benidipine HCl 4.2% | | 0.84% | 0.8% | 0.8% | 0.1% | 0.1% | 10% solid cont. |
| Example 43 | Carvedilol 45.4% | | 7.26% | 9.1% | 7.3% | 0.7% | 1.4% | 10% solid cont. |
| Example 44 | Carvedilol 27.8% | | 4.45% | 4.5% | 4.5% | 0.4% | 0.8% | 10% solid cont. |

TABLE 5-1-continued

Compositions-IV of the pharmaceutical compositions simultaneously having rapid-acting property and long-acting property

| | Ingredient | | | | | | |
|---|---|---|---|---|---|---|---|
| Example 45 | Carvedilol 22.5% | 3.59% | 3.6% | 3.6% | 0.3% | 0.7% | 10% solid cont. |
| Example 46 | Carvedilol 30.3% | 4.84% | 4.8% | 4.8% | 0.4% | 0.9% | 10% solid cont. |
| Example 47 | Carvedilol 30.7% | 4.91% | 4.9% | 4.9% | 0.5% | 0.9% | 10% solid cont. |
| Example 48 | Carvedilol 25.9% | 4.14% | 4.1% | 4.1% | 0.4% | 0.8% | 10% solid cont. |
| Example 49 | Atenolol 43.1% | 8.62% | 8.6% | 8.6% | 0.7% | 1.4% | 10% solid cont. |
| Example 50 | Atenolol 32.9% | 6.57% | 6.6% | 6.6% | 0.5% | 1.1% | 10% solid cont. |

| | | Immediate-release part | | | | | | |
|---|---|---|---|---|---|---|---|---|
| | | Granules | | | | | Additional Excipients | | |
| | | Mixture | | Binding solution | | | | | |
| Ingredient | Active ingredient | Microcrystalline cellulose | Colloidal Silicon Dioxide | Hydroxy propyl cellulose | water | ethanol | Hydroxy propyl cellulose | Croscarmellose sodium | Magnesium Stearate |
| Example 32 | Losartan Potassium 38.4% | 11.5% | 0.4% | 1.0% | 10% solid cont. | | 4.1% | 2.1% | 0.6% |
| Example 33 | Valsartan 46.1% | 13.8% | 0.3% | 1.2% | 10% solid cont. | | 4.3% | 2.1% | 0.6% |
| Example 34 | Telmisartan 34.5% | 10.3% | 0.4% | 0.9% | 10% solid cont. | | 4.1% | 2.0% | 0.6% |
| Example 35 | Olmesartan medoxomil 8.8% | 35.2% | 0.4% | 0.9% | 10% solid cont. | | 4.1% | 2.0% | 0.6% |
| Example 36 | Candesartan cilexetil 11.1% | 41.6% | 0.3% | 2.1% | 10% solid cont. | | 4.2% | 2.1% | 0.6% |
| Example 37 | | | | | | | 3.6% | 1.8% | 0.5% |
| Example 38 | Losartan Potassium 61.3% | 18.4% | 0.6% | 1.6% | 10% solid cont. | | 4.5% | 2.2% | 0.7% |
| Example 39 | Valsartan 64.2% | 19.3% | 0.4% | 1.7% | 10% solid cont. | | 4.5% | 2.3% | 0.7% |
| Example 40 | Telmisartan 59.5% | 17.8% | 0.7% | 1.5% | 10% solid cont. | | 4.5% | 2.2% | 0.7% |
| Example 41 | Olmesartan medoxomil 15.4% | 61.5% | 0.8% | 1.5% | 10% solid cont. | | 4.5% | 2.2% | 0.7% |
| Example 42 | Candesartan cilexetil 16.8% | 62.9% | 0.5% | 3.1% | 10% solid cont. | | 4.5% | 2.3% | 0.7% |
| Example 43 | | | | | | | 3.6% | 1.8% | 0.5% |
| Example 44 | Losartan Potassium 27.8% | 8.4% | 0.3% | 0.7% | 10% solid cont. | | 4.0% | 2.0% | 0.6% |
| Example 45 | Valsartan 35.9% | 10.8% | 0.2% | 0.9% | 10% solid cont. | | 4.1% | 2.1% | 0.6% |
| Example 46 | Telmisartan 24.2% | 7.3% | 0.3% | 0.6% | 10% solid cont. | | 3.9% | 2.0% | 0.6% |
| Example 47 | Olmesartan medoxomil 6.1% | 24.5% | 0.3% | 0.6% | 10% solid cont. | | 3.9% | 2.0% | 0.6% |
| Example 48 | Candesartan cilexetil 8.3% | 31.0% | 0.3% | 1.6% | 10% solid cont. | | 4.0% | 2.0% | 0.6% |
| Example 49 | | | | | | | 3.6% | 1.8% | 0.5% |
| Example 50 | Losartan Potassium 16.4% | 4.9% | 0.2% | 0.4% | 10% solid cont. | | 3.8% | 1.9% | 0.6% |

TABLE 5-1-continued

Compositions-IV of the pharmaceutical compositions simultaneously having rapid-acting property and long-acting property Sustained-release part
Granules

| Ingredient | Active ingredient | Colloidal Silicon Dioxide | Eudragit | Hydroxy ethyl cellulose | Microcrystalline cellulose | Croscarmellose sodium | Hydroxy propyl cellulose | water | Ethanol |
|---|---|---|---|---|---|---|---|---|---|
| | | | Mixture | | | | Binding solution | | |
| Example 51 | Atenolol 28.8% | | 5.76% | 5.8% | 5.8% | 0.5% | 0.9% | 10% solid cont. | |
| Example 52 | Atenolol 34.5% | | 6.90% | 6.9% | 6.9% | 0.6% | 1.1% | 10% solid cont. | |
| Example 53 | Atenolol 34.8% | | 6.95% | 7.0% | 7.0% | 0.6% | 1.1% | 10% solid cont. | |
| Example 54 | Atenolol 31.4% | | 6.29% | 6.3% | 6.3% | 0.5% | 1.0% | 10% solid cont. | |
| Example 55 | Valaciclovir HCl 31.7% | 0.0% | 6.35% | 6.3% | 6.3% | 0.5% | 1.0% | 10% solid cont. | |
| Example 56 | Choline Alfoscerate 41.2% | 0.1% | 8.23% | 8.2% | 8.2% | 0.7% | 1.3% | 10% solid cont. | |
| Example 57 | Acetyl-l-carnitine HCl 41.2% | 0.1% | 8.23% | 8.2% | 8.2% | 0.7% | 1.3% | 10% solid cont. | |
| Example 58 | Venlafaxine HCl 24.4% | | 6.09% | 6.1% | 6.1% | 0.4% | 0.9% | 10% solid cont. | |
| Example 59 | Risperidone 6.8% | | 1.36% | | 1.4% | 0.1% | 0.2% | 10% solid cont. | |
| Example 60 | Quetiapine fumarate 28.0% | | 4.21% | 4.2% | 4.2% | 0.4% | 0.8% | 10% solid cont. | |
| Example 61 | Gabapentin 38.3% | 0.1% | 3.83% | 3.8% | 3.8% | 0.5% | 1.0% | 10% solid cont. | |
| Example 62 | Pregabalin 25.8% | | 3.87% | 7.8% | 3.9% | 0.4% | 0.8% | 10% solid cont. | |
| Example 63 | Levetiracetam 25.8% | 0.1% | 5.16% | 5.2% | 5.2% | 0.4% | 0.8% | 10% solid cont. | |
| Example 64 | Rivastigmine 6.9% | | 0.69% | 1.4% | 1.4% | 0.1% | 0.2% | 10% solid cont. | |
| Example 65 | Aceclofenac 26.5% | | 5.31% | 5.3% | 5.3% | 0.4% | 0.9% | 10% solid cont. | |
| Example 66 | Eperisone HCl 28.7% | | 8.62% | 8.6% | 8.6% | 0.5% | 1.1% | 10% solid cont. | |
| Example 67 | Bepotastine besilate 24.8% | | 6.20% | 6.2% | 6.2% | 0.4% | 0.9% | 10% solid cont. | |
| Example 68 | Metformin HCl 52.4% | 0.1% | 5.24% | 5.2% | 5.2% | 0.7% | 1.4% | 10% solid cont. | |

Immediate-release part
Granules

| Ingredient | Active ingredient | Microcrystalline cellulose | Colloidal Silicon Dioxide | Hydroxy propyl cellulose | water | Ethanol | Hydroxy propyl cellulose | Croscarmellose sodium | Magnesium Stearate |
|---|---|---|---|---|---|---|---|---|---|
| | | Mixture | | Binding solution | | | Additional Excipients | | |
| Example 51 | Valsartan 23.0% | 6.9% | 0.1% | 0.6% | 10% solid cont. | | 3.9% | 2.0% | 0.6% |
| Example 52 | Telmisartan 13.8% | 4.1% | 0.2% | 0.4% | 10% solid cont. | | 3.8% | 1.9% | 0.6% |
| Example 53 | Olmesartan medoxomil 3.5% | 13.9% | 0.2% | 0.3% | 10% solid cont. | | 3.8% | 1.9% | 0.6% |
| Example 54 | Candesartan cilexetil 5.0% | 18.9% | 0.2% | 0.9% | 10% solid cont. | | 3.8% | 1.9% | 0.6% |
| Example 55 | Valaciclovir HCl 15.9% | 4.8% | 0.0% | 0.5% | 10% solid cont. | | 3.7% | 1.8% | 0.6% |

TABLE 5-1-continued

Compositions-IV of the pharmaceutical compositions simultaneously having rapid-acting property and long-acting property

| | | | | | | | | |
|---|---|---|---|---|---|---|---|---|
| Example 56 | | | | | | 3.4% | 1.7% | 0.5% |
| Example 57 | | | | | | 3.4% | 1.7% | 0.5% |
| Example 58 | Venlafaxine HCl 24.4% | 7.3% | 0.2% | 0.8% | 10% solid cont. | 3.8% | 1.9% | 0.6% |
| Example 59 | Risperidone 6.8% | 68.1% | 3.4% | 1.9% | 10% solid cont. | 4.5% | 2.3% | 0.7% |
| Example 60 | Quetiapine fumarate 28.0% | 8.4% | 0.6% | 0.9% | 10% solid cont. | 4.0% | 2.0% | 0.6% |
| Example 61 | Gabapentin 19.2% | 5.7% | 0.0% | 0.6% | 10% solid cont. | 3.8% | 1.9% | 0.6% |
| Example 62 | Pregabalin 25.8% | 7.7% | 0.2% | 0.8% | 10% solid cont. | 3.9% | 1.9% | 0.6% |
| Example 63 | Levetiracetam 25.8% | 7.7% | 0.1% | 0.8% | 10% solid cont. | 3.9% | 1.9% | 0.6% |
| Example 64 | Rivastigmine 6.9% | 68.7% | 1.1% | 1.9% | 10% solid cont. | 4.5% | 2.2% | 0.7% |
| Example 65 | Aceclofenac 26.5% | 8.0% | 0.1% | 0.9% | 10% solid cont. | 4.0% | 2.0% | 0.6% |
| Example 66 | Eperisone HCl 14.4% | 4.3% | 0.1% | 0.5% | 10% solid cont. | 3.8% | 1.9% | 0.6% |
| Example 67 | Bepotastine besilate 24.8% | 7.4% | 1.2% | 0.8% | 10% solid cont. | 3.9% | 2.0% | 0.6% |
| Example 68 | Rosuvastatin calcium 0.5% | 0.3% | 0.1% | 0.0% | 10% solid cont. | 3.6% | 1.8% | 0.5% |

TABLE 5-2

Compositions-IV of the pharmaceutical compositions simultaneously having rapid-acting property and long-acting property

| Sustained-release part spray | First spray | | | | |
|---|---|---|---|---|---|
| | Ethyl Cellulose | Triacetin | Poylethyleneglycol | ethanol 85% | water 15% |
| Example 15 | 7.4% | 1.1% | 1.1% | 6% solid cont. | |
| Example 16 | 17.8% | 2.7% | 2.7% | 6% solid cont. | |
| Example 17 | 17.6% | 2.6% | 2.6% | 6% solid cont. | |
| Example 18 | 16.8% | 2.5% | 2.5% | 6% solid cont. | |
| Example 19 | 15.9% | 2.4% | 2.4% | 6% solid cont. | |
| Example 20 | 17.8% | 2.7% | 2.7% | 6% solid cont. | |
| Example 21 | 3.1% | 0.5% | 0.5% | 6% solid cont. | |
| Example 22 | 3.0% | 0.4% | 0.4% | 6% solid cont. | |
| Example 23 | 2.3% | 0.3% | 0.3% | 6% solid cont. | |
| Example 24 | 11.6% | 1.7% | 1.7% | 6% solid cont. | |
| Example 25 | 10.0% | 1.5% | 1.5% | 6% solid cont. | |
| Example 26 | 13.6% | 2.0% | 2.0% | 6% solid cont. | |
| Example 27 | 13.5% | 2.0% | 2.0% | 6% solid cont. | |
| Example 28 | 11.6% | 1.7% | 1.7% | 6% solid cont. | |
| Example 29 | 10.1% | 1.5% | 1.5% | 6% solid cont. | |
| Example 30 | 13.6% | 2.0% | 2.0% | 6% solid cont. | |
| Example 31 | 17.8% | 2.7% | 2.7% | 6% solid cont. | |
| Example 32 | 7.9% | 1.2% | 1.2% | 6% solid cont. | |
| Example 33 | 5.9% | 0.9% | 0.9% | 6% solid cont. | |
| Example 34 | 8.9% | 1.3% | 1.3% | 6% solid cont. | |
| Example 35 | 9.1% | 1.4% | 1.4% | 6% solid cont. | |
| Example 36 | 7.2% | 1.1% | 1.1% | 6% solid cont. | |
| Example 37 | 17.8% | 2.7% | 2.7% | 6% solid cont. | |
| Example 38 | 2.0% | 0.3% | 0.3% | 6% solid cont. | |
| Example 39 | 1.3% | 0.2% | 0.2% | 6% solid cont. | |
| Example 40 | 2.5% | 0.4% | 0.4% | 6% solid cont. | |
| Example 41 | 2.5% | 0.4% | 0.4% | 6% solid cont. | |
| Example 42 | 1.7% | 0.3% | 0.3% | 6% solid cont. | |
| Example 43 | 17.8% | 2.7% | 2.7% | 6% solid cont. | |
| Example 44 | 10.6% | 1.6% | 1.6% | 6% solid cont. | |
| Example 45 | 8.6% | 1.3% | 1.3% | 6% solid cont. | |
| Example 46 | 11.5% | 1.7% | 1.7% | 6% solid cont. | |

TABLE 5-2-continued

Compositions-IV of the pharmaceutical compositions simultaneously having rapid-acting property and long-acting property

| Sustained-release part spray | First spray | | | |
|---|---|---|---|---|
| | Ethyl Cellulose | Triacetin | Poylethyleneglycol | ethanol 85% / water 15% |
| Example 47 | 11.7% | 1.8% | 1.8% | 6% solid cont. |
| Example 48 | 9.9% | 1.5% | 1.5% | 6% solid cont. |
| Example 49 | 17.8% | 2.7% | 2.7% | 6% solid cont. |
| Example 50 | 13.5% | 2.0% | 2.0% | 6% solid cont. |
| Example 51 | 11.9% | 1.8% | 1.8% | 6% solid cont. |
| Example 52 | 14.2% | 2.1% | 2.1% | 6% solid cont. |
| Example 53 | 14.3% | 2.1% | 2.1% | 6% solid cont. |
| Example 54 | 13.0% | 1.9% | 1.9% | 6% solid cont. |
| Example 55 | 15.7% | 2.4% | 2.4% | 6% solid cont. |
| Example 56 | 20.4% | 3.1% | 3.1% | 6% solid cont. |
| Example 57 | 20.4% | 3.1% | 3.1% | 6% solid cont. |
| Example 58 | 13.2% | 2.0% | 2.0% | 6% solid cont. |
| Example 59 | 2.0% | 0.3% | 0.3% | 6% solid cont. |
| Example 60 | 10.5% | 1.6% | 1.6% | 6% solid cont. |
| Example 61 | 12.8% | 1.9% | 1.9% | 6% solid cont. |
| Example 62 | 12.8% | 1.9% | 1.9% | 6% solid cont. |
| Example 63 | 12.8% | 1.9% | 1.9% | 6% solid cont. |
| Example 64 | 2.7% | 0.4% | 0.4% | 6% solid cont. |
| Example 65 | 10.9% | 1.6% | 1.6% | 6% solid cont. |
| Example 66 | 14.1% | 2.1% | 2.1% | 6% solid cont. |
| Example 67 | 11.2% | 1.7% | 1.7% | 6% solid cont. |
| Example 68 | 17.6% | 2.6% | 2.6% | 6% solid cont. |

TABLE 6

Compositions-V of the pharmaceutical compositions simultaneously having rapid-acting property and long-acting property

| | Example 69 | | Ingredient | |
|---|---|---|---|---|
| Sustained-release part ① | granules ① | Mixture | Acetaminophen | 10.9% |
| | | | Tramadol HCl | 6.3% |
| | | | Colloidal Silicon Dioxide | 0.04% |
| | | | Eudragit | 2.3% |
| | | | Hydroxyethylcellulose | 2.3% |
| | | | Microcrystalline cellulose | 2.3% |
| | | | Croscarmellose sodium | 0.3% |
| | | Binding solution | Hydroxypropylcellulose | 0.2% |
| | | | Sodium Lauryl Sulfate | 0.3% |
| | | | Water (30%) Ethanol (70%) | 12.4% solid cont. |
| | First spray | | Ethyl Cellulose | 2.5% |
| | | | NaOH | 0.04% |
| | | | Triacetin | 0.4% |
| | | | Poylethyleneglycol | 0.3% |
| | | | Water (10%) Ethanol (90%) | 6% solid cont. |
| | Second spray | | Hydroxyethylcellulose | 1.3% |
| | | | Hydroxypropylmethylcellulose | 0.2% |
| | | | Water (15%) Ethanol (85%) | 6% solid cont. |

TABLE 6-continued

Compositions-V of the pharmaceutical compositions simultaneously having rapid-acting property and long-acting property

| | | | Example 69 Ingredient | |
|---|---|---|---|---|
| | | Third spray | Ethyl Cellulose | 4.7% |
| | | | Triacetin | 0.7% |
| | | | Poylethyleneglycol | 0.7% |
| | | | Water (10%) Ethanol (90%) | 6% solid cont. |
| Sustained-release part ② | granules ② | Mixture | Acetaminophen | 24.6% |
| | | | Colloidal Silicon Dioxide | 0.1% |
| | | | Eudragit | 3.40% |
| | | Binding solution | Ethyl Cellulose | 0.2% |
| | | | Water (30%) Ethanol (70%) | 9% solid cont. |
| | | Forth spray | Ethyl Cellulose | 4.7 |
| | | | Triacetin | 0.7 |
| | | | Poylethyleneglycol | 0.7 |
| | | | Water (10%) Ethanol (90%) | 6% solid cont. |
| Immediate-release part | Granules | Mixture | Acetaminophen | 19.0% |
| | | | Colloidal Silicon Dioxide | 0.1% |
| | | | Powdered Cellulose | 5.90% |
| | | | Croscarmellose sodium | 2.5% |
| | | Binding solution | Polyvinylpyrrolidone | 1.3% |
| | | | Water (100%) | 7.1% solid cont. |
| | | Additional Excipients | Croscarmellose sodium | 0.4% |
| | | | Magnesium Stearate | 0.4% |

EXPERIMENTAL EXAMPLES

Dissolutoin Test of the Pharmaceutical Composition of the Present Invention

1) Experimental Method

For the tablets prepared in the above Examples, dissolution test was performed. Specifically, the dissolution test was performed for 6 hours under conditions of 50 rotations/min using pH 1.2, pH 6.8 or water as a dissolution medium according to a dissolution test second method of general test method of Korean Pharmacopoeia (Korean Food and Drug Administration, 9$^{th}$ edition, p1172). The dissolution solution was taken each 5 ml at 15, 30, 45, 60, 90, 120, 180, 240, 300, 360, 480 and 600 minutes after initiation of the dissolution test and filtered, the filtrate was used as a test solution and analyzed by HPLC, and the results are shown in FIGS. 1 to 15, At this time, Tylenol ER tablet (Janssen Korea Ltd.: containing acetaminophen 650 mg, dual-layered tablet) which is a representative drug simultaneously having a rapid-acting property and a long-acting property was used as Comparative Example.

2) Experimental Results

As shown in FIGS. 1 to 16, it can be seen that the pharmaceutical composition of the present invention simultaneously has a rapid-acting property and a long-acting property because the sustained-release part and the immediate-release part are independently controlled, and it is not sensitive to pH change and it may be used without limitation to the kinds of drugs.

Specifically, FIG. 1 shows the results of dissolution test of the composition of <Example 1-1> in water over time, and it is confirmed that acetaminophen contained in the sustained-release part and the immediate-release part is linearly sustained-released and immediately released, and Tramadol HCl contained only in the sustained-release part is sustained-released.

Figure 2:
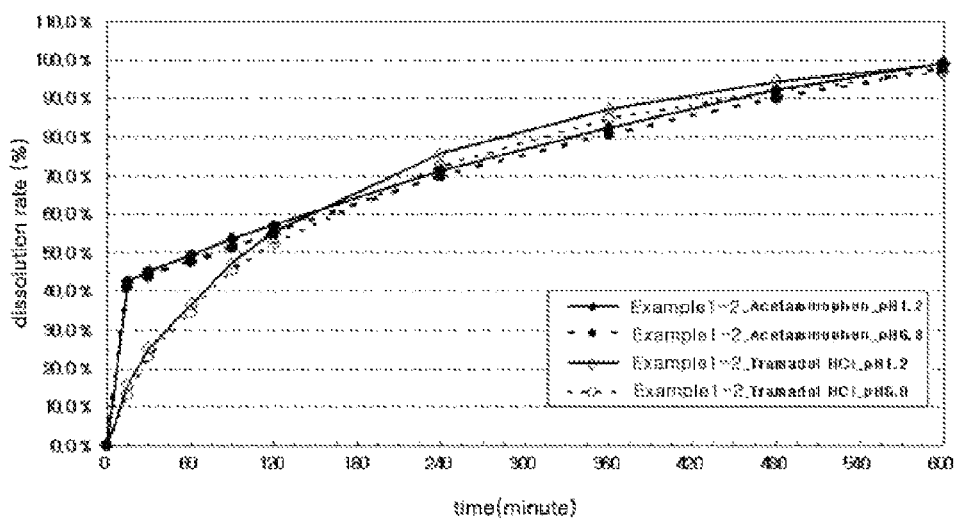
FIG. 2 shows dissolution rates of Tramadol HCl and Acetaminophen of the pharmaceutical composition of the present invention with the composition of <Example 1-2> at pH 1.2 and pH 6.8 over time.

FIG. 2 shows the results of dissolution test of the composition of <Example 1-2> at pH 1.2 and pH 6.8 over time, and it is confirmed that in the composition having different compositions of hydroxyethylcellulose and Eudragit from the sustained-release granules of <Example 1-1>, Tramadol HCl contained only in the sustained-release part and acetaminophen contained in the sustained-release part and the immediate-release part are sustained-released and immediately released without being affected by pH change.

Figure 3:
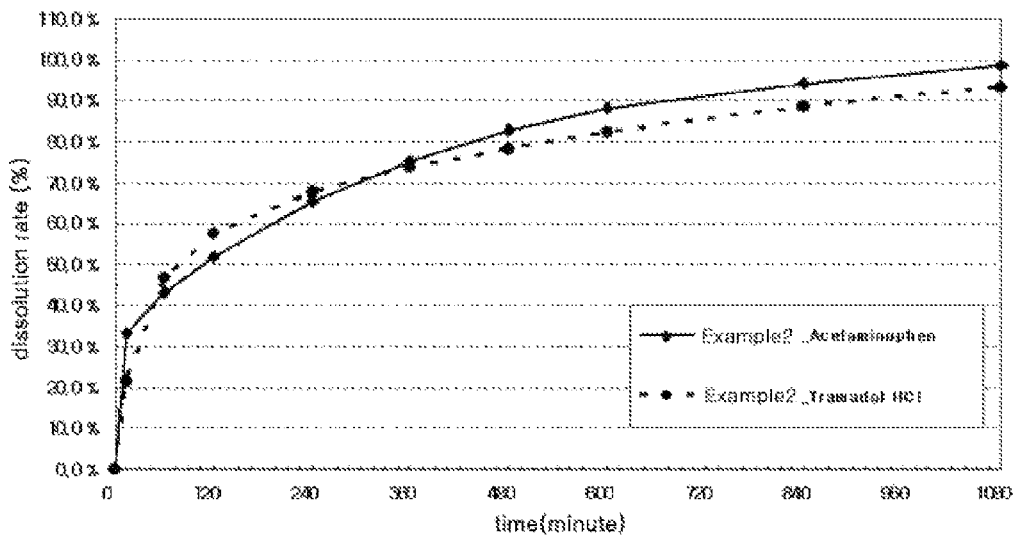
FIG. 3 shows dissolution rate of the pharmaceutical composition of the present invention with the composition of <Example 2> in water over time.

FIG. 3 shows the results of dissolution test of the composition of <Example 2> in water over time, and it is confirmed that in case the sustained-release part is granulated only with water-insoluble polymer, acetaminophen contained in the sustained-release part and the immediate-release part is sustained-released and immediately released, and Tramadol HCl contained only in the sustained-release part is released with high initial dissolution rate.

Figure 4:
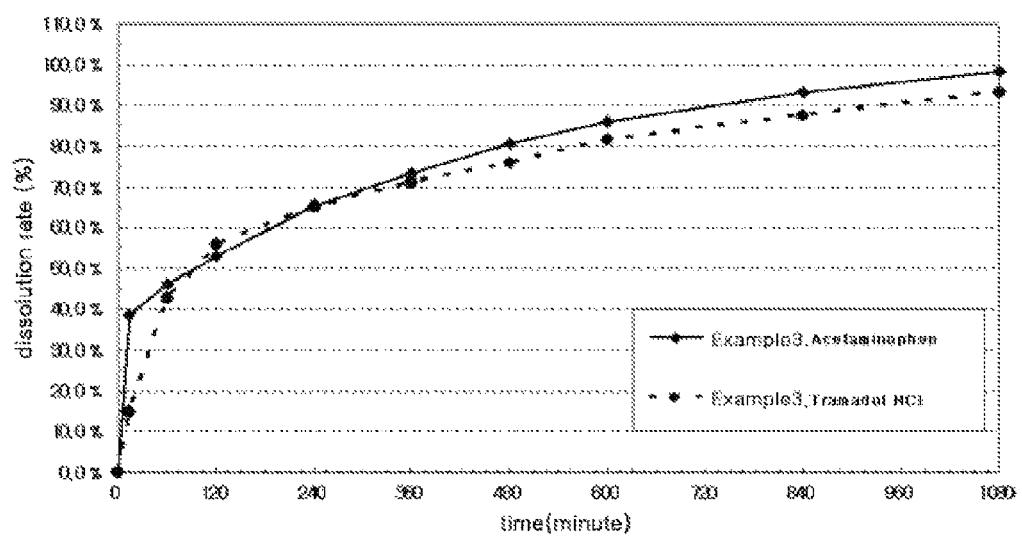
FIG. 4 shows dissolution rate of the pharmaceutical composition of the present invention with the composition of <Example 3> in water over time.

FIG. 4 shows the results of dissolution test of the composition of <Example 3> in water over time, and it is confirmed that in case hydrophilic delivery vector polyethyleneglycol is added to the sustained-release second spray solution compared to <Example 2>, acetaminophen contained in the sustained-release part and the immediate-release part is sustained-released and immediately released, and Tramadol HCl contained only in the sustained-release part is sustained-released.

Figure 5:
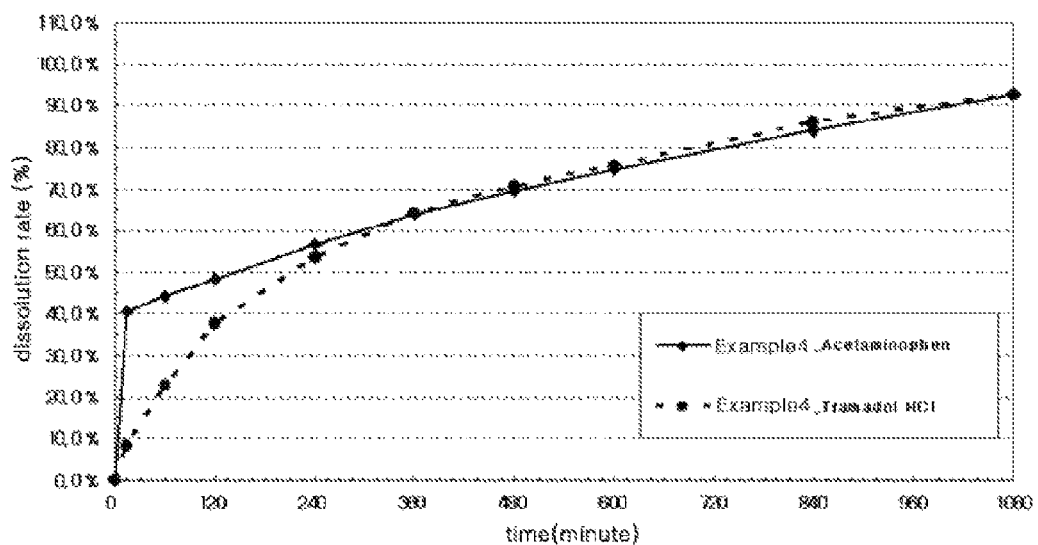
FIG. 5 shows dissolution rate of the pharmaceutical composition of the present invention with the composition of <Example 4> in water over time.

FIG. 5 shows the results of dissolution results of the composition of <Example 4> in water over time, and it is confirmed that in case the sustained-release part is granulated with microcrystalline cellulose and hydroxypropylcellulose, acetaminophen contained in the sustained-release part and the immediate-release part is sustained-released and immediately released, and Tramadol HCl contained only in the sustained-release part is sustained-released.

Figure 6:
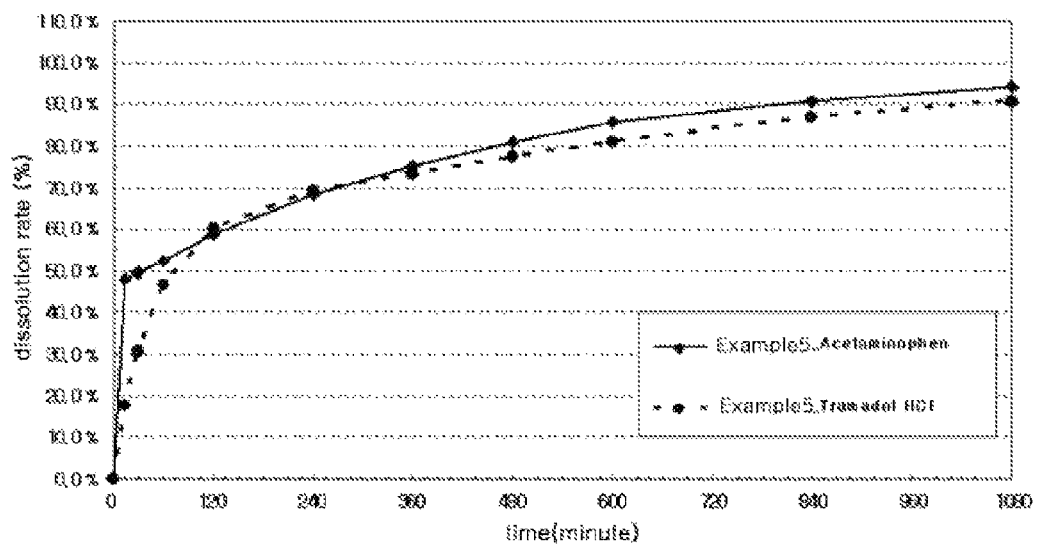
FIG. 6 shows dissolution rate of the pharmaceutical composition of the present invention with the composition of <Example 5> in water over time.

FIG. 6 shows the results of dissolution test of the composition of <Example 5> in water over time, and it is confirmed that in case talc is excluded from the spray solution coated on the sustained-release granules, acetaminophen contained in the sustained-release part and the immediate-release part is sustained-released and immediately released, and Tramadol HCl contained only in the sustained-release part is sustained-released.

Figure 7:
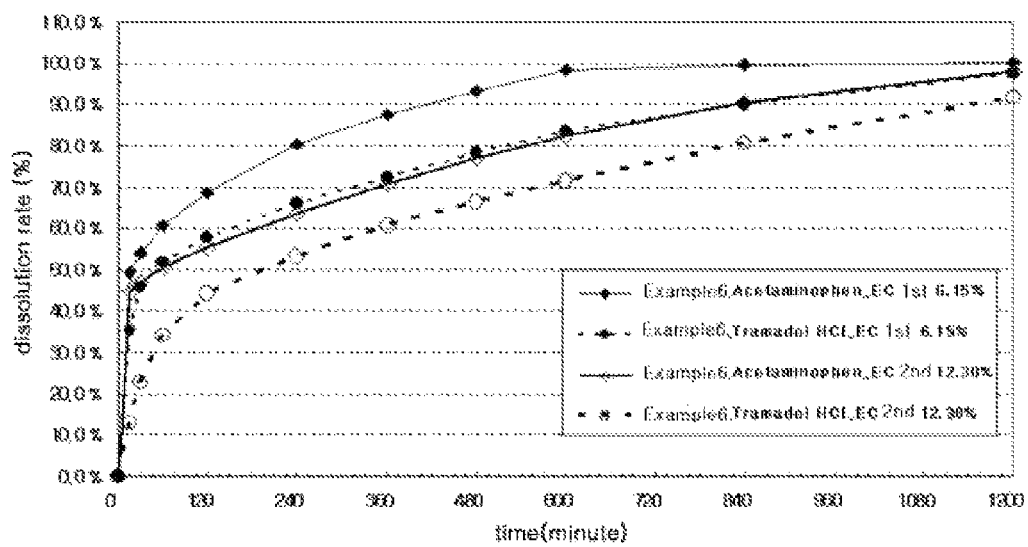
FIG. 7 shows dissolution rate of the pharmaceutical composition of the present invention with the composition of <Example 6> in water according to time and the spray amount of the water-insoluble base.

FIG. 7 shows the results of dissolution test of the composition of <Example 6> in water over time, and it is confirmed that acetaminophen contained in the sustained-release part and the immediate-release part is sustained-released and immediately released, and Tramadol HCl contained only in the sustained-release part is sustained-released. Particularly, it is confirmed that the sustained-release and immediate-release amounts of acetaminophen and Tramadol HCl may be controlled by controlling the amount of water-insoluble polymer ethylcellulose coated on the sustained-release part.

Figure 8:
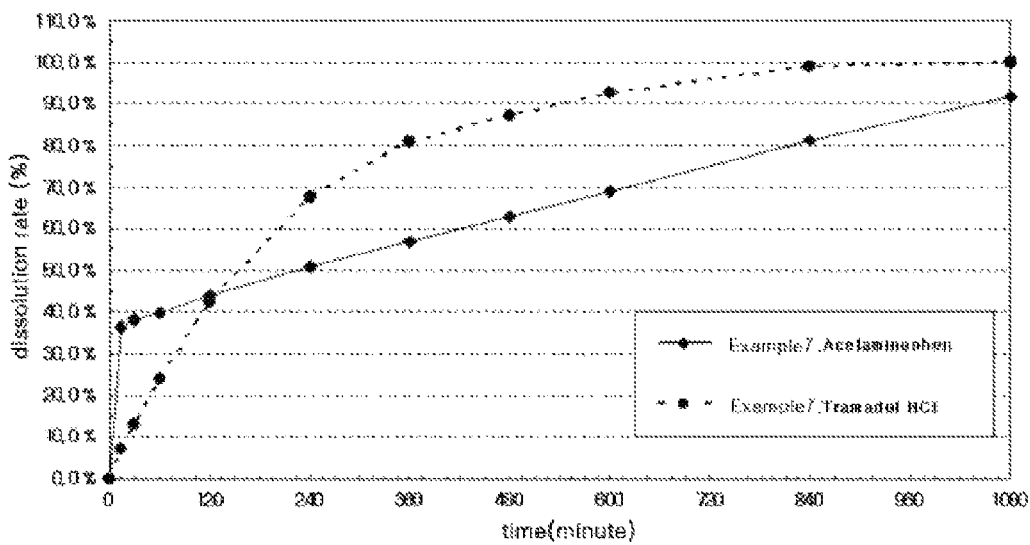
FIG. 8 shows dissolution rate of the pharmaceutical composition of the present invention with the composition of <Example 7> in water over time.

FIG. 8 shows the results of dissolution test of the composition of <Example 7> in water over time, and it is confirmed that in case sodium lauryl sulfate and calcium carbonate are excluded from the sustained-release granules, acetaminophen contained in the sustained-release part and the immediate-release part is sustained-released and immediately released, and Tramadol HCl contained only in the sustained-release part is sustained-released.

Figure 9:
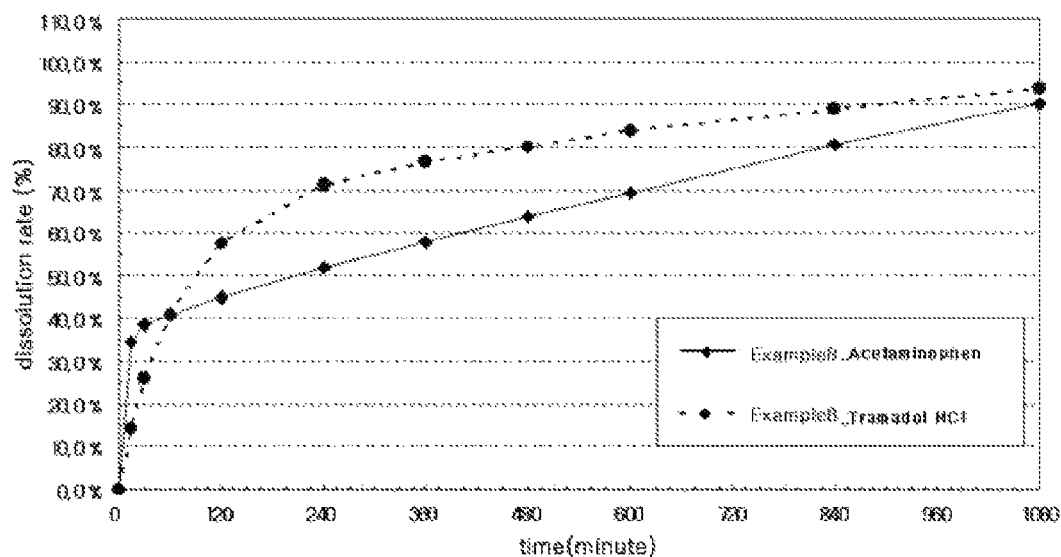
FIG. 9 shows dissolution rate of the pharmaceutical composition of the present invention with the composition of <Example 8> in water over time.

FIG. 9 shows the results of dissolution test of the composition of <Example 8> in water over time, and it is confirmed that in case acetaminophen and Tramadol HCl are separately granulated in the sustained-release part, acetaminophen contained in the sustained-release part and the immediate-release part is sustained-released and immediately released, and Tramadol HCl contained only in the sustained-release part is sustained-released.

Figure 10:
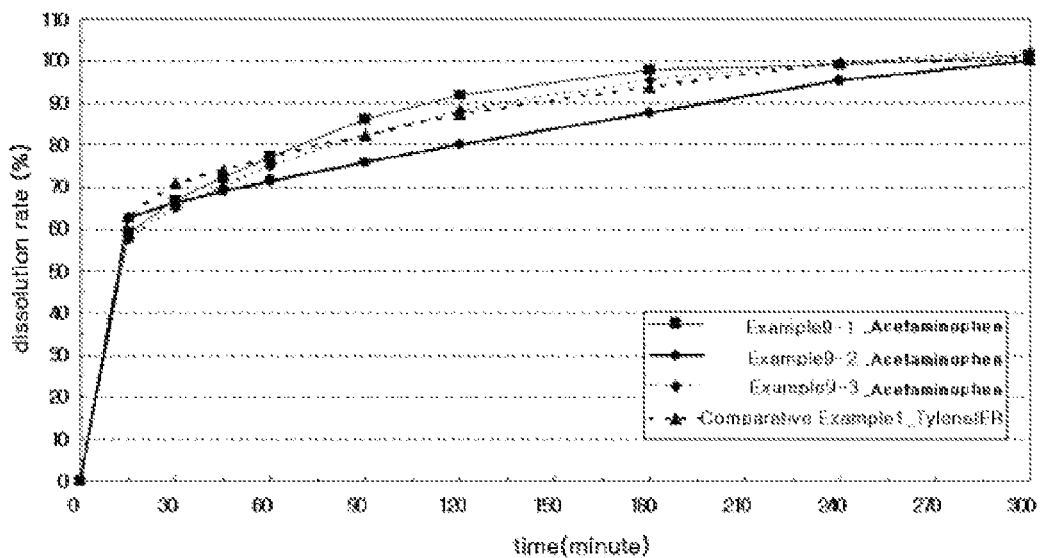
FIG. 10 shows dissolution rates of the pharmaceutical compositions of the present invention with the compositions of <Example 9-1> and <Example 9-3> in water over time (Comparative Example: Tylenol ER).

FIG. 10 shows the results of dissolution test of the compositions of <Example 9-1> to <Example 9-3> in water over time, and it is confirmed that in case the kind of a base is changed in the mixture constituting the sustained-release granules, acetaminophen contained in the sustained-release part and the immediate-release part exhibits very similar release pattern to Tylenol ER.

FIG. 11 and FIG. 12 show the results of dissolution test of the compositions of <Example 10> and <Example 11> in water over time, and it is confirmed that in case the immediate-release part and the sustained-release part are composed at a ratio of 3:2 <Example 10> and at a ratio of 2:3 <Example 11>, acetaminophen contained in the sustained-release part and the immediate-release part is sustained-released and immediately released, and Tramadol HCl contained only in the sustained-release part is sustained-released.

FIG. 13 shows the results of dissolution test of the composition of <Example 12> in water over time, and it is confirmed that Niacin contained in the sustained-release part and the immediate-release part is sustained-released and immediately released, and rosuvastatin contained only in the immediate-release part is immediately released.

FIG. 14 shows the results of dissolution test of the composition of <Example 13> in water over time, and it is confirmed that Niacin contained in the sustained-release part and the immediate-release part is sustained-released and immediately released, and pitavastatin contained only in the immediate-release part is immediately released.

FIG. 15 shows the results of dissolution test of the composition of <Example 14> in water over time, and it is confirmed that Niacin contained in the sustained-release part and the immediate-release part is sustained-released and immediately released, and atrovastatin contained only in the immediate-release part is immediately released.

FIG. 16 shows the results of dissolution test of the composition of <Example 69> at pH 6.8 over time, and the following Table 7 and Table 8 show the results of dissolution test of the compositions of <Example 15> to <Example 40> and <Example 41> to <Example 69> at pH 6.8 over time, and it is confirmed that the active ingredients contained in the sustained-release part are sustained-released and the active ingredients contained only in the immediate-release part are immediately released.

As explained, according to the pharmaceutical composition of the present invention, problems of delay in disintegration or delay in release of the active ingredients of the immediate-release part due to the influence of the sustained-release part may not be caused, the sustained-release part and the immediate-release part may exhibit independent release properties, and the contents or kinds of the active ingredients requiring immediate-release or sustained-release are not limited because the active ingredients are contained respectively in the sustained-release part and the immediate-release part and independently released, and stable dissolution property may be obtained even at pH change, and thus, improved therapeutic effect may be anticipated.

TABLE 7

| | | Dissolution rate at pH 6.8 under conditions of second method 50 rpm over time (%) | | | | | |
|---|---|---|---|---|---|---|---|
| Example | Ingredients | 0 min | 30 min | 60 min | 180 min | 360 min | 600 min |
| 15 | Rebamipide | 0.0% | 59.7% | 65.2% | 75.3% | 90.0% | 99.0% |
| 16 | Metformin HCl | 0.0% | 25.1% | 39.4% | 70.9% | 88.8% | 97.2% |
| 17 | Glimepiride | 0.0% | 44.2% | 60.1% | 66.4% | 70.2% | |
| | Metformin HCl | 0.0% | 25.1% | 39.4% | 70.9% | 88.8% | 97.2% |
| 18 | Pioglitazone HCl | 0.0% | 0.5% | 0.7% | 1.0% | 1.2% | 1.4% |
| | Metformin HCl | 0.0% | 25.1% | 39.4% | 70.9% | 88.8% | 97.2% |
| 19 | Sitagliptin phosphate monohydrate | 0.0% | 15.0% | 23.8% | 26.9% | 29.5% | 34.2% |
| | Metformin HCl | 0.0% | 25.1% | 39.4% | 70.9% | 88.8% | 97.2% |
| 20 | Voglibose | 0.0% | 42.3% | 58.9% | 85.7% | 93.4% | 99.8% |
| | Metformin HCl | 0.0% | 25.1% | 39.4% | 70.9% | 88.8% | 97.2% |
| 21 | Voglibose | 0.0% | 30.3% | 44.9% | 77.6% | 90.9% | 99.1% |
| 22 | Glimepiride | 0.0% | 44.2% | 60.1% | 66.4% | 70.2% | |
| | Voglibose | 0.0% | 30.3% | 44.9% | 77.6% | 90.9% | 99.1% |
| 23 | Pioglitazone HCl | 0.0% | 0.5% | 0.7% | 1.0% | 1.2% | 1.4% |
| | Voglibose | 0.0% | 30.3% | 44.9% | 77.6% | 90.9% | 99.1% |
| 24 | Levosulpiride | 0.0% | 32.1% | 42.6% | 68.9% | 92.7% | 98.7% |
| 25 | Mosapride citrate | 0.0% | 33.2% | 45.1% | 70.6% | 88.9% | 99.0% |

TABLE 7-continued

| | | Dissolution rate at pH 6.8 under conditions of second method 50 rpm over time (%) | | | | | |
|---|---|---|---|---|---|---|---|
| Example | Ingredients | 0 min | 30 min | 60 min | 180 min | 360 min | 600 min |
| 26 | Trimebutine | 0.0% | 30.6% | 40.8% | 66.7% | 85.8% | 98.8% |
| 27 | Itopride HCl | 0.0% | 34.8% | 46.7% | 72.5% | 90.3% | 99.9% |
| 28 | Cilostazol | 0.0% | 43.2% | 48.6% | 54.6% | 64.7% | 75.7% |
| 29 | Limaprost Alpha-Cyclodextrin Clathrate | 0.0% | 27.6% | 30.6% | 37.2% | 48.5% | 60.6% |
| 30 | Sarpogrelate HCl | 0.0% | 30.2% | 35.4% | 45.2% | 59.7% | 75.0% |
| 31 | Nifedipine | 0.0% | 3.3% | 6.8% | 20.5% | 37.8% | 59.7% |
| 32 | Losartan Potassium | 0.0% | 99.3% | | | | |
| | Nifedipine | 0.0% | 3.3% | 6.8% | 20.5% | 37.8% | 59.7% |
| 33 | Valsartan | 0.0% | 50.1% | 69.9% | 85.6% | 93.7% | 99.2% |
| | Nifedipine | 0.0% | 3.3% | 6.8% | 20.5% | 37.8% | 59.7% |
| 34 | Telmisartan | 0.0% | 43.6% | 62.4% | 76.8% | 87.1% | 97.5% |
| | Nifedipine | 0.0% | 3.3% | 6.8% | 20.5% | 37.8% | 59.7% |
| 35 | Olmesartan medoxomil | 0.0% | 98.1% | | | | |
| | Nifedipine | 0.0% | 3.3% | 6.8% | 20.5% | 37.8% | 59.7% |
| 36 | Candesartan cilexetil | 0.0% | 0.0% | 0.2% | 0.4% | | |
| | Nifedipine | 0.0% | 3.3% | 6.8% | 20.5% | 37.8% | 59.7% |
| 37 | Benidipine HCl | 0.0% | 4.5% | 7.6% | 25.2% | 45.1% | 70.9% |
| 38 | Losartan Potassium | 0.0% | 99.3% | | | | |
| | Benidipine HCl | 0.0% | 4.5% | 7.6% | 25.2% | 45.1% | 70.9% |
| 39 | Valsartan | 0.0% | 50.1% | 69.9% | 85.6% | 93.7% | 99.2% |
| | Benidipine HCl | 0.0% | 4.5% | 7.6% | 25.2% | 45.1% | 70.9% |
| 40 | Telmisartan | 0.0% | 43.6% | 62.4% | 76.8% | 87.1% | 97.5% |
| | Benidipine HCl | 0.0% | 4.5% | 7.6% | 25.2% | 45.1% | 70.9% |

TABLE 8

| | | Dissolution rate at pH 6.8 under conditions of second method 50 rpm over time (%) | | | | | |
|---|---|---|---|---|---|---|---|
| Example | Ingredient | 0 min | 30 min | 60 min | 180 min | 360 min | 600 min |
| 41 | Olmesartan medoxomil | 0.0% | 98.1% | | | | |
| | Benidipine HCl | 0.0% | 4.5% | 7.6% | 25.2% | 45.1% | 70.9% |
| 42 | Candesartan cilexetil | 0.0% | 0.0% | 0.2% | 0.4% | | |
| | Benidipine HCl | 0.0% | 4.5% | 7.6% | 25.2% | 45.1% | 70.9% |
| 43 | Carvedilol | 0.0% | 5.7% | 8.4% | 27.1% | 48.6% | 73.8% |
| 44 | Losartan Potassium | 0.0% | 99.3% | | | | |
| | Carvedilol | 0.0% | 5.7% | 8.4% | 27.1% | 48.6% | 73.8% |
| 45 | Valsartan | 0.0% | 50.1% | 69.9% | 85.6% | 93.7% | 99.2% |
| | Carvedilol | 0.0% | 5.7% | 8.4% | 27.1% | 48.6% | 73.8% |
| 46 | Telmisartan | 0.0% | 43.6% | 62.4% | 76.8% | 87.1% | 97.5% |
| | Carvedilol | 0.0% | 5.7% | 8.4% | 27.1% | 48.6% | 73.8% |
| 47 | Olmesartan medoxomil | 0.0% | 98.1% | | | | |
| | Carvedilol | 0.0% | 5.7% | 8.4% | 27.1% | 48.6% | 73.8% |
| 48 | Candesartan cilexetil | 0.0% | 0.0% | 0.2% | 0.4% | | |
| | Carvedilol | 0.0% | 5.7% | 8.4% | 27.1% | 48.6% | 73.8% |
| 49 | Atenolol | 0.0% | 8.2% | 13.4% | 30.5% | 46.3% | 60.1% |
| 50 | Losartan Potassium | 0.0% | 99.3% | | | | |
| | Atenolol | 0.0% | 8.2% | 13.4% | 30.5% | 46.3% | 60.1% |
| 51 | Valsartan | 0.0% | 50.1% | 69.9% | 85.6% | 93.7% | 99.2% |
| | Atenolol | 0.0% | 8.2% | 13.4% | 30.5% | 46.3% | 60.1% |
| 52 | Telmisartan | 0.0% | 43.6% | 62.4% | 76.8% | 87.1% | 97.5% |
| | Atenolol | 0.0% | 8.2% | 13.4% | 30.5% | 46.3% | 60.1% |
| 53 | Olmesartan medoxomil | 0.0% | 98.7% | | | | |
| | Atenolol | 0.0% | 8.2% | 13.4% | 30.5% | 46.3% | 60.1% |
| 54 | Candesartan cilexetil | 0.0% | 0.0% | 0.2% | 0.4% | | |
| | Atenolol | 0.0% | 8.2% | 13.4% | 30.5% | 46.3% | 60.1% |
| 55 | Valaciclovir HCl | 0.0% | 35.1% | 39.4% | 50.0% | 63.2% | 72.7% |
| 56 | Choline Alfoscerate | 0.0% | 25.0% | 41.7% | 71.5% | 88.3% | 98.4% |
| 57 | Acetyl-l-carnitine HCl | 0.0% | 31.3% | 46.8% | 70.1% | 87.9% | 98.0% |
| 58 | Venlafaxine HCl | 0.0% | 52.4% | 57.8% | 63.9% | 74.1% | 85.6% |
| 59 | Risperidone | 0.0% | 52.0% | 53.0% | 58.6% | 67.9% | 78.8% |
| 60 | Quetiapine | 0.0% | 51.9% | 58.3% | 64.7% | 76.9% | 88.4% |
| 61 | Gabapentin | 0.0% | 34.8% | 36.2% | 50.6% | 63.4% | 72.8% |
| 62 | Pregabalin | 0.0% | 52.6% | 55.7% | 60.2% | 70.5% | 81.3% |
| 63 | Levetiracetam | 0.0% | 51.5% | 59.1% | 66.0% | 78.1% | 90.2% |
| 64 | Rivastigmine | 0.0% | 52.1% | 55.2% | 60.6% | 68.9% | 81.0% |
| 65 | Aceclofenac | 0.0% | 51.3% | 58.0% | 63.9% | 74.1% | 87.7% |
| 66 | Eperisone HCl | 0.0% | 36.1% | 38.6% | 52.6% | 66.1% | 76.4% |
| 67 | Bepotastine besilate | 0.0% | 52.6% | 55.1% | 59.8% | 68.7% | 79.8% |

TABLE 8-continued

| | | Dissolution rate at pH 6.8 under conditions of second method 50 rpm over time (%) | | | | | |
|---|---|---|---|---|---|---|---|
| Example | Ingredient | 0 min | 30 min | 60 min | 180 min | 360 min | 600 min |
| 68 | Rosuvastatin calcium | 0.0% | 99.9% | | | | |
| | Metformin HCl | 0.0% | 25.1% | 39.4% | 70.9% | 88.8% | 97.2% |
| 69 | Acetaminophen | 0.0% | 51.7% | 60.4% | 78.1% | 91.8% | 98.0% |
| | Tramadol HCl | 0.0% | 27.1% | 41.9% | 71.1% | 88.9% | 96.3% |

What is claimed is:

1. A pharmaceutical composition comprising
a sustained-release part, comprising one or more selected from the group consisting of acetaminophen and tramadol as a first active pharmaceutical ingredient, a water-soluble viscous polymer or a mixture of water-soluble viscous polymer and water-insoluble polymer as a release control base, and a pharmaceutically acceptable carrier,
wherein the sustained-release part has a coating on the surface thereof,
wherein the coating consists of a first coating comprising a water-soluble viscous polymer, and a second coating comprising a mixture of a water-insoluble polymer and one or more selected from the group consisting of Talc, Triacetin and Triethylcitrate on the first coating, or the coating consists of a first coating comprising a water-insoluble polymer, a second coating comprising a water-soluble viscous polymer on the first coating, and a third coating comprising a mixture of an additional water-insoluble polymer and one or more selected from the group consisting of Talc, Triacetin and Triethylcitrate on the second coating,
wherein the water-insoluble polymer exhibits solubility of 0.01 g/ml or more in an aqueous solvent at any pH, and is one or more selected from the group consisting of ethylcellulose, microcrystalline cellulose and methacrylate-ethylacrylate based copolymer,
wherein the water-soluble viscous polymer exhibits solubility of 0.01 g/ml or more in an aqueous solvent at any pH, and absorbs an aqueous solvent in an aqueous solution of 10% w/v, 20° C. to exhibit viscosity change of 1 mPas or more, based on the dry state, and is one or more selected from the group consisting of hydroxylalkylcellulose and hydroxypropylalkylcellulose; and
an immediate release part comprising one or more selected from the group consisting of acetaminophen and tramadol as a second active pharmaceutical ingredient and a pharmaceutically acceptable carrier,
wherein the sustained-release part and the immediate-release part are in the form of independent granules, and the granules are mixed.

2. The pharmaceutical composition of claim 1, wherein the pharmaceutical composition is in the form of a tablet.

3. The pharmaceutical composition of claim 1, wherein:
the second coating comprising a mixture of a water-insoluble polymer and one or more selected from the group consisting of Talc, Triacetin and Triethylcitrate additionally comprises polyethylene glycol,
the first coating comprising a water-insoluble polymer additionally comprises polyethylene glycol, or
the third coating comprising a mixture of an additional water-insoluble polymer and one or more selected from the group consisting of Talc, Triacetin and Triethylcitrate additionally comprises polyethylene glycol.

4. The pharmaceutical composition of claim 3, wherein the pharmaceutical composition is in the form of a tablet.

5. The pharmaceutical composition of claim 1, wherein the composition additionally comprises the second sustained-release part in the form of independent granules, coated with a water-insoluble polymer on the surface, comprising a mixture of a first active pharmaceutical ingredient, and water-insoluble polymer as a release control base, and a pharmaceutically acceptable carrier.

6. The pharmaceutical composition of claim 5, wherein the water-insoluble polymer coated on the surface of the second sustained-release part additionally comprises one or more selected from the group consisting of talc, triacetin, triethylcitrate, and polyethylene glycol.

7. The pharmaceutical composition of claim 5, wherein the pharmaceutical composition is in the form of a tablet.

* * * * *